United States Patent
Kuhr et al.

(10) Patent No.: US 7,074,519 B2
(45) Date of Patent: Jul. 11, 2006

(54) MOLEHOLE EMBEDDED 3-D CROSSBAR ARCHITECTURE USED IN ELECTROCHEMICAL MOLECULAR MEMORY DEVICE

(75) Inventors: Werner G. Kuhr, Oak Hills, CA (US); David F. Bocian, Riverside, CA (US); Zhiming Liu, Riverside, CA (US); Amir Yasseri, Riverside, CA (US)

(73) Assignee: The Regents of the University of California, Oakland, CA (US)

( * ) Notice: Subject to any disclaimer, the term of this patent is extended or adjusted under 35 U.S.C. 154(b) by 233 days.

(21) Appl. No.: 10/046,499

(22) Filed: Oct. 26, 2001

(65) Prior Publication Data

US 2003/0082444 A1 May 1, 2003

(51) Int. Cl.
*G11C 11/00* (2006.01)
*G11C 13/00* (2006.01)

(52) U.S. Cl. .................. 429/149; 365/151; 365/153

(58) Field of Classification Search ............... 429/149, 429/164, 213, 231.8, 218.1, 152, 153; 365/151, 365/153; 204/403.01, 403.03; 205/794.5
See application file for complete search history.

(56) References Cited

U.S. PATENT DOCUMENTS

| | | | |
|---|---|---|---|
| 3,637,581 A | | 1/1972 | Horiguchi et al. |
| 4,618,509 A | | 10/1986 | Bulkowski |
| 5,280,183 A | | 1/1994 | Batzel et al. |
| 5,463,014 A | | 10/1995 | Epstein et al. |
| 5,475,075 A | | 12/1995 | Brant et al. |
| 5,476,797 A | * | 12/1995 | Matsunaga .............. 436/513 |
| 5,512,131 A | * | 4/1996 | Kumar et al. ............ 438/738 |
| 5,547,774 A | | 8/1996 | Gimzewski et al. |
| 5,622,872 A | * | 4/1997 | Ribi ........................ 436/518 |
| 5,814,420 A | | 9/1998 | Chu |
| 5,844,055 A | | 12/1998 | Brandt et al. |
| 5,922,537 A | * | 7/1999 | Ewart et al. .................. 435/6 |
| 5,942,388 A | * | 8/1999 | Willner et al. ............... 435/6 |
| 6,013,170 A | | 1/2000 | Meade |
| 6,031,756 A | | 2/2000 | Gimzewski et al. |
| 6,066,448 A | * | 5/2000 | Wohlstadter et al. ........ 435/6 |
| 6,128,214 A | | 10/2000 | Kuekes et al. |
| 6,132,685 A | * | 10/2000 | Kercso et al. ............. 422/104 |
| 6,300,141 B1 | * | 10/2001 | Segal et al. ............. 435/287.1 |
| 6,324,091 B1 | | 11/2001 | Gryko et al. |
| 6,381,169 B1 | | 4/2002 | Bocian et al. |
| 6,451,942 B1 | | 9/2002 | Li et al. |

FOREIGN PATENT DOCUMENTS

WO    WO 97/05477    *   2/1997

OTHER PUBLICATIONS

Ball et al., Electrochemistry in Nanovials Fabricated by Combining Screen Printing and Laser Micromachining, Anal. Chem. (2000) 72:497–501.

Bratten et al., Micromachining Sensors for Electrochemical Measurement in Subnanoliter Volumes, Anal. Chem. (1997) 69:253–258.

(Continued)

*Primary Examiner*—Gregg Cantelmo
(74) *Attorney, Agent, or Firm*—Quine I.P. Law Group, P.C.; Tom Hunter

(57) ABSTRACT

This invention provides a new design and fabrication for a three-dimensional crossbar architecture embedding a submicron or nanometer sized hole (called a molehole) in each cross-region. Each molehole is an electrochemical cell consisting of two or more sectional surfaces separated by a non-conductor (e.g. a dialectric layer and solid electrolyte). When used in electrochemical molecular memory device (EMMD), the architecture provides unique features such as a nano-scale electroactive surface, no interaction between memory elements, and easier miniaturization and integration.

19 Claims, 6 Drawing Sheets

OTHER PUBLICATIONS

Clark et al., Characterization of Electrochemical Responses in Picoliter Volumes, Anal. Chem. (1998) 70:1119–1125.

Clark et al., Electrochemical Analysis in Picoliter Microvials, Anal. Chem. (1997) 69:259–263.

Gavin et al., Continuous Separations with Microfabricated Electrophoresis–Electrochemical Array Detection, J. Am. Chem. Soc. (1986) 118:8932–8936.

Kovach et al., Faradaic Electrochemistry at Microcylinder, Band and Tubular Band Electrodes, J. Electroanal. Chem., (1985) 185:285–295.

Hyde et al., Ellipsometric Measurements of the Pt–Aqueous Electrolyte Interface, in the Absence and in the Presence of Specific Anionic Adsorption, (1985) 186:267–286.

Nagale et al., Individually Addressable, Submicrometer Band Electrode Arrays. 1. Fabrication from Multilayered Materials, Anal. Chem. (1998) 70:2902–2907.

"Ferrocene—Molecule of the Month" Jun. 1996, University of Oxford Web Page, http://www.ncl.ox.ac.uk/mom/ferrocene/ferrocene2.html.

"Ferrocene—Synthesis", Jun. 1996, University of Oxford Web Page, http://www.ncl.ox.ac.uk/mom/ferrocene/synthesis.html.

Buchler and Ng (2000) In *The Porphyrin Handbook, vol. 3*, pp. 245–294, Eds. K. M. Kadish, K. M. Smith, R. Guilard, Academic Press, San Diego, CA.

Chabach et al. (1996) "Mixed–Metal Triple–Decker Sandwich Complexes with the Porphyrin/Phthalocynine/Porphyrin Ligand System" *Angew. Chem. Int. Ed. Engl.*, 35: 898.

Cotton et al (1976) Basic Inorganic Chemistry, pp. 125, 497, 518.

Duchowski et al. (1990) Spectroscopic Characerization of Triple Decker Lanthanide Porphyrin Sandwich Complexes. Effects of Strong $\pi\pi$ Interactions in Extended Assemblies J Am. Chem. Soc. 112: 8807–8811.

Gorman (1997) "Encapsulated Electroactive Molecules" Adv. Mater. 9(14) 1117–1119.

Gorman (1999) "Molecular Structure–Property Relationships for Electron–Transfer Rate Attenuation in Redox–Active Core Dendrimers" J. Am. Chem. Soc. 121: 9958–9966.

Gross (2001) "Investigation of Rational Synthesis of Heteroleptic Porphyrinic Lanthanide (Europium, Cerium) Triple–Decker Sandwich Complexes" Inorg. Chem. 40: 4762–4774.

Gryko (2000) "Synthesis of Thiol–Derivatized Ferrocene–Porphrins for Studies of Multibit Information Storage" J. Org. Chem. 65: 7356–7362.

Gryko (2001) "Studies Related to the Design and Synthesis of a Molecular Octal Counter" J. Mater. Chem. 11: 1162–1180.

Jiang et al. (1998) "Heteroleptic Triple–Decker (Phthalocyaninato)–Porphyrinato) Europium (III) Complexes: Synthesis and Electrochemical Study" Inorganica Chimca Acta 268: 49–53.

Li et al. (2000) "Synthesis of Thiol–Derivatized Europium Porphyrinic Triple–Decker Sandwich Complexes for Multibit Molecular Information Storage" J. Org. Chem. 65: 7379–7390.

Roth (2000) "Molecular Approach Toward Information Storage Based on the Redox Properties of Porphyrins in Self–Assembled Monolayers" J. Vac. Sci. Technol. B. 18(5) 2359–2364.

Ruben et al. (2000) "Multilevel Molecular Electronic Species: Electrochemical Reduction of a [2×2] Co4 Grid Type Complex by 11 Electrons in 10 Reversible Steps" Angew. Chem. Int. Ed. 39(22) 4139–4142.

Sommerauer et al. (1996) "Separation of 1(3), 9(10), 16(17), 23(24)–Tetrasubstituted Phthalycyanines with Newly Developed HPLC Phases" J. Am. Chem. Soc. 118: 10085–10093.

Wong et al. (1974) "Lanthanide Polyphyrin Complexes, A Potential New Class of Nuclear Magnetic Resonance Dipolar Probe" J. Am. Chem. Soc. 96(22) 7149–7150.

\* cited by examiner

Fabrication procedures of molecular well-embedded architectures

MOLEHOLE EMBEDDED 3-D CROSSBAR ARCHITECTURE USED IN ELECTROCHEMICAL MOLECULAR MEMORY DEVICE

STATEMENT AS TO RIGHTS TO INVENTIONS MADE UNDER FEDERALLY SPONSORED RESEARCH AND DEVELOPMENT

This invention was made with Government support under Grant No: N00014-99-0357 awarded by the Office of Naval Research. The Government of the United States of America may have certain rights in this invention.

CROSS-REFERENCE TO RELATED APPLICATIONS

[Not Applicable]

FIELD OF THE INVENTION

This invention pertains to the fields of microelectronics and molecular electronics. In particular this invention involves the design and fabrication of a novel architecture that can be used for a molecular electrochemical memory device or for a sensor array.

BACKGROUND OF THE INVENTION

There has been a great interest in the development of nanoliter to picoliter microvials in analytical chemistry. Arrays of vials containing nanoliter to picoliter volumes have been etched in silicon for sample introduction in capillary electrophoresis and mass spectroscopy (Clark and Ewing (1998) *Anal. Chem.*, 70: 1119–1125; Clark et al. (1997) *Anal. Chem.*, 69: 259–263).

Previous approaches, however, have not provided a convenient method of regulating the relative surface area of the electrodes exposed in the vials, have not been convenient for the fabrication of large precisely arranged arrays of such vials, or have not been feasible for the preparation of sub micron structures.

SUMMARY OF THE INVENTION

In one embodiment, this invention provides a nanoscale electrochemical cell. In preferred embodiments, the cell comprises a well having a cross-sectional area typically less than about 1 micron by 1 micron (e.g. 1 $\mu m^2$), preferably less than 100 nm by 100 nm, more preferably less than about 50 nm by 50 nm, and most preferably less than about 25 nm by 25 nm. A wall of the well comprises a first electrode and, optionally, a second electrode. The first electrode and second electrode are separated by a non-conductor or semiconductor, and the ratio of the surface area of the first electrode exposed to the interior of the well to the surface area of the second electrode exposed to the interior of said well is at least about 2:1, preferably at least about 5:1, and more preferably at least 10:1 or 20:1. The ratio is typically predetermined (e.g. determined prior to fabrication of the well). In preferred embodiments, the well has a volume less than about 100 femtoliters, more preferably less than about 50 femtoliters, and most preferably less than about 10 or 5 femtoliters.

In certain embodiments, the first electrode and said second electrode comprises all the walls comprising the well except the bottom wall and, if present, a top wall. In certain embodiments, the first electrode comprises all the walls comprising the well. The first and/or second electrode can comprise a material selected from the group consisting of copper, silver, chromium, gold, platinum, a conducting polymer, aluminum, silicon, germanium, gallium arsenide, ruthenium, titanium, tantalum, carbon nanotubes, carbon nanoribbons, etc. The first and/or second electrode can be a semiconductor (e.g. n- or p-doped silicon, germanium, etc.). In particularly preferred embodiments, the insulator or semiconductor is an insulator (e.g., silicon dioxide, silicon nitride, etc.).

In particularly preferred embodiments, the second and/or first electrode is coupled to a molecule (e.g. a redox-active molecule, a binding partner, etc.). The molecule (e.g. redox-active molecule) is directly electrically coupled to the electrode or is electrically coupled to the electrode through a linker. The coupling can be covalent (e.g. through a sulfer, through an oxygen, through a linker bearing a sulfer, through a linker bearing an oxygen, etc.). Preferred redox-active molecules include, but are not limited to a porphyrinic macrocycle, a metallocene, a linear polyene, a cyclic polyene, a heteroatom-substituted linear polyene, a heteroatom-substituted cyclic polyene, a tetrathiafulvalene, a tetraselenafulvalene, a metal coordination complex, a buckyball, a triarylamine, a 1,4-phenylenediamine, a xanthene, a flavin, a phenazine, a phenothiazine, an acridine, a quinoline, a 2,2'-bipyridyl, a 4,4'-bipyridyl, a tetrathiotetracene, and a peri-bridged naphthalene dichalcogenide. Particularly preferred redox-active molecules include, but are not limited to, a porphyrin, an expanded porphyrin, a contracted porphyrin, a ferrocene, a linear porphyrin polymer, a porphyrinic sandwich comples, and a porphyrin array. In certain embodiments the redox-active molecule comprises a porphyrinic macrocycle substituted at a β-position or at a meso-position.

In certain embodiments, the second and/or first electrode has electrically coupled thereto a binding partner (e.g. a nucleic acid, a protein, an antibody, a lectin, a carbohydrate, a glycoprotein, any post-translationally-modified protein, etc.).

In certain particularly preferred embodiments, the first electrode is a silver electrode, said second electrode is a gold electrode. The second electrode can have has coupled thereto a redox-active molecule and/or a binding partner, e.g. as described above and herein. In certain embodiments, the cell is formed on a group IV element substrate (e.g. Si, Ge, doped Si, doped Ge, etc.).

In another embodiment, this invention provides an electrochemical cell array. In preferred embodiments, the cell array comprises a plurality of nanoscale electrochemical cells as described herein. Different wells comprising the array can have the same or different electrodes and/or electrode surface areas. In preferred embodiments, the array comprises one or more wells having a volume less than about 100 femtoliters, more preferably less than about 50 femtoliters, and most preferably less than about 10 or 5 femtoliters. A preferred array comprises at least two well, more preferably at least about 10 wells, still more preferably at least about 50 or 100 wells, and most preferably at least about 500, 1000, 10000, 100000, or 1000000 wells. In particularly preferred embodiments, the center to center distance between two wells comprising the array is about 2.5 microns or less, more preferably about 250 nm or less, and most preferably about 200, 150, 100, or 50 nm or less. In certain embodiments, a plurality of the cells comprising the array are independently addressable. Different cells can have conductors made of the same or different materials. The cells can comprise, 1, 2, at least 3, preferably at least 4, still more preferably at least 5 or more conductors. One or more cells comprising the array can have a molecule coupled to one or more electrodes (e.g. the second electrode) comprising the cell. Preferred molecules include, but are not limited to redox-active molecules and/or binding partners, e.g., as described herein. Different cells comprising the array can have the same molecule or different molecules electrically coupled therein.

In still another embodiment, this invention provides a molecular memory. In preferred embodiments, the molecular memory comprises one or more nanoscale electrochemical cells (e.g. an electrochemical cell array). Preferred electrochemical cells and/or electrochemical cell arrays include those cells or cell arrays described herein where one or more redox-active species is electrically coupled to one or more electrodes comprising a nanoscale electrochemical cell. Preferred redox-active species include, but are not limited to those identified herein, e.g. a porphyrinic macrocycle, a metallocene, a linear polyene, a cyclic polyene, a heteroatom-substituted linear polyene, a heteroatom-substituted cyclic polyene, a tetrathiafulvalene, a tetraselenafulvalene, a metal coordination complex, a buckyball, a triarylamine, a 1,4-phenylenediamine, a xanthene, a flavin, a phenazine, a phenothiazine, an acridine, a quinoline, a 2,2'-bipyridyl, a 4,4'-bipyridyl, a tetrathiotetracene, a peri-bridged naphthalene dichalcogenide, etc. Preferred memory devices comprise at least 100, more preferably at least about 1000, still more preferably at least about 10,000 and most preferably at least about 100,000 or 1,000,000 electrochemical cells. In particularly preferred embodiments, the a plurality of the cells comprising the memory are independently addressable.

The memory device, e.g. one or more cells comprising the memory device, can be coupled to various integrated circuit elements (e.g. a transistor, a diode, a rectifier, a capacitor, a logic gate, etc.). In certain embodiments, one or more cells comprising the memory device can be coupled to a voltage source for reading and/or setting the oxidation state of the cell(s). The memory device can be a component of a computer system.

In another embodiment, this invention provides a sensor, e.g. for detecting one or more analytes. In preferred embodiments, the molecular memory comprises one or more nanoscale electrochemical cells (e.g. an electrochemical cell array). Preferred electrochemical cells and/or electrochemical cell arrays include those cells or cell arrays described herein where one or more binding partners (e.g., a nucleic acid, a protein, an antibody, a lectin, a carbohydrate, a glycoprotein, any post-translationally-modified protein, etc.) are electrically coupled to one or more electrodes comprising a nanoscale electrochemical cell. In certain embodiments, the sensor comprises at least two different binding partners, each species of binding partner in a different well. In certain embodiments, the sensor comprises at least five, preferably at least ten different binding partners, each species of binding partner in a different well. Preferred sensors comprise at least 2, or 5, preferably at least about 10, more preferably at least about 100 or 1000, still more preferably at least about 10,000 and most preferably at least about 100,000 or 1,000,000 electrochemical cells. One or more wells (cells) comprising the sensor can be in fluid communication with a microchannel.

In still yet another embodiment, this invention provides a method of making a nanoscale electrochemical cell. The method involves depositing on a non-conducting substrate a first conductor; depositing on the conductor a semiconductor or a nonconductor; depositing on the semiconductor or a nonconductor a second conductor; and forming a hole through the second conductor, the nonconductor or semiconductor, and into or through the first conductor, whereby the hole forms a well having a cross-sectional area cross-sectional area typically less than about 1 micron by 1 micron (e.g. 1 $\mu m^2$), preferably less than 100 nm by 100 nm, more preferably less than about 50 nm by 50 nm, and most preferably less than about 25 nm by 25 nm, and the first conductor, and/or the insulator or semiconductor, and/or the second conductor comprise a wall and/or floor of the well. Preferred non-conducting substrates include, but are not limited to silicon dioxide, silicon nitride, and the like. In certain embodiments, the first and/or the second conductor is deposited by electron beam evaporation, thermal evaporation, electrochemical reduction, or electroless deposition. In certain embodiments, depositing the first and/or second conductor comprises depositing a layer of conducting material and selectively removing regions of said conducting material to form a patterned conducting material. The selective removing can comprise placing a patterned resist on the conductor and then etching said conductor. In any of the cells described herein, the conductor can be comprised of one or more conducting materials. Similarly, in any of the cells described herein, the insulating or semiconducting material can be—comprised of one or more insulating and/or semiconducting materials. In certain embodiments, the first conductor comprises a silver layer. In certain embodiments, the second conductor comprises a gold layer. In certain embodiments, thenonconductor or semiconductor comprises a dielectric. In preferred embodiments, the hole is formed by a method selected from the group consisting of laser drilling, RIE techniques, CAIBM techniques, wet etching.

The method can additionally comprise coupling a molecule (e.g. a redox active molecule, a binding partner, etc.) to the said second and/or to the first conductor. The hole can be one of a plurality of holes. In certain embodiments, the ratio of the surface area of said first conductor exposed to the interior of said well to the surface area of said second conductor exposed to the interior of said well is at least is at least about 2:1, preferably at least about 5:1, and more preferably at least 10:1 or 20:1. The ratio can be predetermined. The wells fabricated according to this method include, but need not be limited to, any of the wells or cell arrays described herein.

In still another embodiment, this invention comprises kits comprising an electrochemical memory device and/or a sensor device, and/or materials for fabricating an electrochemical memory device, and/or materials for fabricating a sensor device. Preferred kits include a substrate comprising an electrochemical cell or electrochemical cell array as described herein. The kits can additionally include redox active molecules and/or binding partners, and/or reagents or coupling the redox-active molecules and/or binding partners in a cell as described herein.

Definitions

The term "oxidation" refers to the loss of one or more electrons in an element, compound, or chemical substituent/subunit. In an oxidation reaction, electrons are lost by atoms of the element(s) involved in the reaction. The charge on these atoms must then become more positive. The electrons are lost from the species undergoing oxidation and so electrons appear as products in an oxidation reaction. An oxidation is taking place in the reaction $Fe^{2+}(aq) \rightarrow Fe^{3+}(aq)+e^-$ because electrons are lost from the species being oxidized, $Fe^{2+}(aq)$, despite the apparent production of electrons as "free" entities in oxidation reactions. Conversely the term reduction refers to the gain of one or more electrons by an element, compound, or chemical substituent/subunit.

An "oxidation state" refers to the electrically neutral state or to the state produced by the gain or loss of electrons to an element, compound, or chemical substituent/subunit. In a preferred embodiment, the term "oxidation state" refers to states including the neutral state and any state other than a neutral state caused by the gain or loss of electrons (reduction or oxidation).

The term "multiple oxidation states" means more than one oxidation state. In preferred embodiments, the oxidation states may reflect the gain of electrons (reduction) or the loss of electrons (oxidation).

The terms "different and distinguishable" when referring to two or more oxidation states means that the net charge on the entity (atom, molecule, aggregate, subunit, etc.) can exist in two different states. The states are said to be "distinguishable" when the difference between the states is greater than thermal energy at room temperature (e.g. 0° C. to about 40° C.).

The term "tightly coupled" when used in reference to a subunit of a multi-subunit (e.g., polymeric) storage molecule of this invention refers to positioning of the subunits relative to each other such that oxidation of one subunit alters the oxidation potential(s) of the other subunit. In a preferred embodiment the alteration is sufficient such that the (non-neutral) oxidation state(s) of the second subunit are different and distinguishable from the non-neutral oxidation states of the first subunit. In a preferred embodiment the tight coupling is achieved by a covalent bond (e.g. single, double, triple, etc.). However, in certain embodiments, the tight coupling can be through a linker, via an ionic interaction, via a hydrophobic interaction, through coordination of a metal, or by simple mechanical juxtaposition. It is understood that the subunits could be so tightly coupled that the redox processes are those of a single supermolecule.

The term "electrode" refers to any medium capable of transporting charge (e.g. electrons) to and/or from a storage molecule. Preferred electrodes are metals or conductive organic molecules. The electrodes can be manufactured to virtually any 2-dimensional or 3-dimensional shape (e.g. discrete lines, pads, planes, spheres, cylinders, etc.).

The term "fixed electrode" is intended to reflect the fact that the electrode is essentially stable and unmovable with respect to the storage medium. That is, the electrode and storage medium are arranged in an essentially fixed geometric relationship with each other. It is of course recognized that the relationship alters somewhat due to expansion and contraction of the medium with thermal changes or due to changes in conformation of the molecules comprising the electrode and/or the storage medium. Nevertheless, the overall spatial arrangement remains essentially invariant. In a preferred embodiment this term is intended to exclude systems in which the electrode is a movable "probe" (e.g. a writing or recording "head", an atomic force microscope (AFM) tip, a scanning tunneling microscope (STM) tip, etc.).

The term "working electrode" is used to refer to one or more electrodes that are used to set or read the state of a storage medium and/or storage molecule.

The term "reference electrode" is used to refer to one or more electrodes that provide a reference (e.g. a particular reference voltage) for measurements recorded from the working electrode. In preferred embodiments, the reference electrodes in a memory device of this invention are at the same potential although in some embodiments this need not be the case.

The term "electrically coupled" when used with reference to a storage molecule and/or storage medium and electrode refers to an association between that storage medium or molecule and the electrode such that electrons move from the storage medium/molecule to the electrode or from the electrode to the storage medium/molecule and thereby alter the oxidation state of the storage medium/molecule. Electrical coupling can include direct covalent linkage between the storage medium/molecule and the electrode, indirect covalent coupling (e.g. via a linker), direct or indirect ionic bonding between the storage medium/molecule and the electrode, or other bonding (e.g. hydrophobic bonding). In addition, no actual bonding may be required and the storage medium/molecule may simply be contacted with the electrode surface. There also need not necessarily be any contact between the electrode and the storage medium/molecule where the electrode is sufficiently close to the storage medium/molecule to permit electron tunneling between the medium/molecule and the electrode.

The term "redox-active unit" or "redox-active subunit" refers to a molecule or component of a molecule that is capable of being oxidized or reduced by the application of a suitable voltage.

The term "redox-active" molecule refers to a molecule or component of a molecule that is capable of being oxidized or reduced by the application of a suitable voltage.

The term "subunit", as used herein, refers to a redox-active component of a molecule.

The terms "storage molecule" or "memory molecule" refer to a molecule having one or more oxidation states that can be used for the storage of information (e.g. a molecule comprising one or more redox-active subunits). Preferred storage molecules have two or more different and distinguishable non-neutral oxidation states.

The term "storage medium" refers to a composition comprising two or more storage molecules. The storage medium can contain only one species of storage molecule or it can contain two or more different species of storage molecule. In preferred embodiments, the term "storage medium" refers to a collection of storage molecules. Preferred storage media comprise a multiplicity (at least 2) of different and distinguishable (preferably non-neutral) oxidation states. The multiplicity of different and distinguishable oxidation states can be produced by the combination of different species of storage molecules, each species contributing to said multiplicity of different oxidation states and each species having a single non-neutral oxidation state. Alternatively or in addition, the storage medium can comprise one or more species of storage molecule having a multiplicity of non-neutral oxidation states. The storage medium can contain predominantly one species of storage molecule or it can contain a number of different storage molecules. The storage media can also include molecules other than storage molecules (e.g. to provide chemical stability, suitable mechanical properties, to prevent charge leakage, etc.).

The term "electrochemical cell" typically refers to a reference electrode, a working electrode, a redox-active molecule (e.g. a storage medium), and, if necessary, some means (e.g., a dielectric) for providing electrical conductivity between the electrodes and/or between the electrodes and the medium. In some embodiments, the dielectric is a component of the storage medium.

The terms "memory element", "memory cell", or "storage cell" refer to an electrochemical cell that can be used for the storage of information. Preferred "storage cells" are discrete regions of storage medium addressed by at least one and preferably by two electrodes (e.g. a working electrode and a reference electrode). The storage cells can be individually addressed (e.g. a unique electrode is associated with each memory element) or, particularly where the oxidation states of different memory elements are distinguishable, multiple memory elements can be addressed by a single electrode. The memory element can optionally include a dielectric (e.g. a dielectric impregnated with counterions).

The term "storage location" refers to a discrete domain or area in which a storage medium is disposed. When addressed with one or more electrodes, the storage location may form a storage cell. However if two storage locations contain the same storage media so that they have essentially the same oxidation states, and both storage locations are commonly addressed, they may form one functional storage cell.

"Addressing" a particular element refers to associating (e.g., electrically coupling) that memory element with an electrode such that the electrode can be used to specifically determine the oxidation state(s) of that memory element.

The terms "read" or "interrogate" refer to the determination of the oxidation state(s) of one or more molecules (e.g. molecules comprising a storage medium).

The term "refresh" when used in reference to a storage molecule or to a storage medium refers to the application of a voltage to the storage molecule or storage medium to re-set the oxidation state of that storage molecule or storage medium to a predetermined state (e.g. an oxidation state the storage molecule or storage medium was in immediately prior to a read).

The term "$E_{1/2}$" refers to the practical definition of the formal potential (E°) of a redox process as defined by $E=E°+(RT/nF)\ln(D_{ox}/D_{red})$ where R is the gas constant, T is temperature in K (Kelvin), n is the number of electrons involved in the process, F is the Faraday constant (96,485 Coulomb/mole), $D_{ox}$ is the diffusion coefficient of the oxidized species and $D_{red}$ is the diffusion coefficient of the reduced species.

A "voltage source" is any source (e.g. molecule, device, circuit, etc.) capable of applying a voltage to a target (e.g. an electrode).

The phrase "output of an integrated circuit" refers to a voltage or signal produced by a one or more integrated circuit(s) and/or one or more components of an integrated circuit.

A "voltammetric device" is a device capable of measuring the current produced in an electrochemical cell as a result of the application of a voltage or change in voltage.

An "amperometric device" is a device capable of measuring the current produced in an electrochemical cell as a result of the application of a specific potential field potential ("voltage").

A "potentiometric device" is a device capable of measuring potential across an interface that results from a difference in the equilibrium concentrations of redox molecules in an electrochemical cell.

A "coulometric device" is a device capable of the net charge produced during the application of a potential field ("voltage") to an electrochemical cell.

An "impedance spectrometer" is a device capable of determining the overall impedance of an electrochemical cell.

A "sinusoidal voltammeter" is a voltammetric device capable of determining the frequency domain properties of an electrochemical cell.

The term "porphyrinic macrocycle" refers to a porphyrin or porphyrin derivative. Such derivatives include porphyrins with extra rings ortho-fused, or ortho-perifused, to the porphyrin nucleus, porphyrins having a replacement of one or more carbon atoms of the porphyrin ring by an atom of another element (skeletal replacement), derivatives having a replacement of a nitrogen atom of the porphyrin ring by an atom of another element (skeletal replacement of nitrogen), derivatives having substituents other than hydrogen located at the peripheral (meso-, β-) or core atoms of the porphyrin, derivatives with saturation of one or more bonds of the porphyrin (hydroporphyrins, e.g., chlorins, bacteriochlorins, isobacteriochlorins, decahydroporphyrins, corphins, pyrrocorphins, etc.), derivatives obtained by coordination of one or more metals to one or more porphyrin atoms (metalloporphyrins), derivatives having one or more atoms, including pyrrolic and pyrromethenyl units, inserted in the porphyrin ring (expanded porphyrins), derivatives having one or more groups removed from the porphyrin ring (contracted porphyrins, e.g., corrin, corrole) and combinations of the foregoing derivatives (e.g. phthalocyanines, sub-phthalocyanines, and porphyrin isomers). Preferred porphyrinic macrocycles comprise at least one 5-membered ring.

The term "porphyrin" refers to a cyclic structure typically composed of four pyrrole rings together with four nitrogen atoms and two replaceable hydrogens for which various metal atoms can readily be substituted. A typical porphyrin is hemin.

The term "multiporphyrin array" refers to a discrete number of two or more covalently-linked porphyrinic macrocycles. The multiporphyrin arrays can be linear, cyclic, or branched.

The terms "sandwich coordination compound" or "sandwich coordination complex" refer to a compound of the formula $L_nM^{n-1}$, where each L is a heterocyclic ligand (as described below), each M is a metal, n is 2 or more, most preferably 2 or 3, and each metal is positioned between a pair of ligands and bonded to one or more hetero atom (and typically a plurality of hetero atoms, e.g., 2, 3, 4, 5) in each ligand (depending upon the oxidation state of the metal). Thus sandwich coordination compounds are not organometallic compounds such as ferrocene, in which the metal is bonded to carbon atoms. The ligands in the sandwich coordination compound are generally arranged in a stacked orientation (i.e., are generally cofacially oriented and axially aligned with one another, although they may or may not be rotated about that axis with respect to one another) (see, e.g., Ng and Jiang (1997) *Chemical Society Reviews* 26: 433–442). Sandwich coordination complexes include, but are not limited to "double-decker sandwich coordination compound" and "triple-decker sandwich coordination compounds". The synthesis and use of sandwich coordination compounds is described in detail in U.S. Pat. No. 6,212,093B1.

The term "double-decker sandwich coordination compound" refers to a sandwich coordination compound as described above where n is 2, thus having the formula $L^1$-$M^1$-$L^2$, wherein each of $L^1$ and $L^2$ may be the same or different (see, e.g., Jiang et al. (1999) *J. Porphyrins Phthalocyanines* 3: 322–328).

The term "triple-decker sandwich coordination compound" refers to a sandwich coordination compound as described above where n is 3, thus having the formula $L^1$-$M^1$ $L^2$-$M^2$-$L^3$, wherein each of $L^1$, $L^2$ and $L^3$ may be the same or different, and $M^1$ and $M^2$ may be the same or different (see, e.g., Arnold et al. (1999) *Chemistry Letters* 483–484).

A "linker" is a molecule used to couple two different molecules, two subunits of a molecule, or a molecule to a substrate.

A "substrate" is a, preferably solid, material suitable for the attachment of one or more molecules. Substrates can be formed of materials including, but not limited to glass, plastic, silicon, germanium, minerals (e.g. quartz), semiconducting materials (e.g. doped silicon, doped germanium, etc.), ceramics, metals, etc.

The term "aryl" refers to a compound whose molecules have the ring structure characteristic of benzene, naphthalene, phenanthrene, anthracene, etc. (i.e., either the 6-carbon ring of benzene or the condensed 6-carbon rings of the other aromatic derivatives). For example, an aryl group may be phenyl or naphthyl ($C_{10}H_9$). It is recognized that the aryl group, while acting as substituent can itself have additional substituents (e.g. the substituents provided for $S''$ in the various Formulas herein).

The term "alkyl" refers to a paraffinic hydrocarbon group which may be derived from an alkane by dropping one hydrogen from the formula. Examples are methyl ($CH_3$—), ethyl ($C_2H_5$—), propyl ($CH_3CH_2CH_2$—), isopropyl (($CH_3)_2CH$—).

The term "halogen" refers to one or the electronegative elements of group VIIB of the periodic table (fluorine, chlorine, bromine, iodine, astatine).

The term "nitro" refers to the $NO_2$ group.

The term "amino" refers to the $NH_2$ group.

The term "perfluoroalkyl" refers to an alkyl group where every hydrogen atom is replaced with a fluorine atom.

The term "perfluoroaryl" refers to an aryl group where every hydrogen atom is replaced with a fluorine atom.

The term "pyridyl" refers to an aryl group where one CH unit is replaced with a nitrogen atom.

The term "cyano" refers to the —CN group.

The term "thiocyanato" refers to the —SCN group.

The term "sulfoxyl" refers to a group of composition RS(O)— where R is some alkyl, aryl, cycloalkyl, perfluoroalkyl, or perfluoroaryl group. Examples include, but are not limited to methylsulfoxyl, phenylsulfoxyl, etc.

The term "sulfonyl" refers to a group of composition $RSO_2$— where R is some alkyl, aryl, cycloalkyl, perfluoroalkyl, or perfluoroaryl group. Examples include, but are not limited to methylsulfonyl, phenylsulfonyl, p-toluenesulfonyl, etc.

The term "carbamoyl" refers to the group of composition $R^1(R^2)NC(O)$— where $R^1$ and $R^2$ are H or some alkyl, aryl, cycloalkyl, perfluoroalkyl, or perfluoroaryl group. Examples include, but are not limited to N-ethylcarbamoyl, N,N-dimethylcarbamoyl, etc The term "amido" refers to the group of composition $R^1CON(R^2)$— where $R^1$ and $R^2$ are H or some alkyl, aryl, cycloalkyl, perfluoroalkyl, or perfluoroaryl group. Examples include, but are not limited to acetamido, N-ethylbenzamido, etc.

The term "acyl" refers to an organic acid group in which the OH of the carboxyl group is replaced by some other substituent (RCO—). Examples include, but are not limited to acetyl, benzoyl, etc.

In preferred embodiments, when a metal is designated by "M" or "M'''", where n is an integer, it is recognized that the metal may be associated with a counterion.

The term "substituent" as used in the formulas herein, particularly designated by S or $S''$ where n is an integer, in a preferred embodiment refer to redox-active groups (subunits) that can be used to adjust the redox potential(s) of the subject compound. Preferred substituents include, but are not limited to, aryl, phenyl, cycloalkyl, alkyl, halogen, alkoxy, alkylthio, perfluoroalkyl, perfluoroaryl, pyridyl, cyano, thiocyanato, nitro, amino, alkylamino, acyl, sulfoxyl, sulfonyl, amido, and carbamoyl. In preferred embodiments, a substituted aryl group is attached to a porphyrin or a porphyrinic macrocycle, and the substituents on the aryl group are selected from the group consisting of aryl, phenyl, cycloalkyl, alkyl, halogen, alkoxy, alkylthio, perfluoroalkyl, perfluoroaryl, pyridyl, cyano, thiocyanato, nitro, amino, alkylamino, acyl, sulfoxyl, sulfonyl, amido, and carbamoyl.

Particularly preferred substituents include, but are not limited to, 4-chlorophenyl, 3-acetamidophenyl, 2,4-dichloro-4-trifluoromethyl). Preferred substituents provide a redox potential range of less than about 5 volts, preferably less than about 2 volts, more preferably less than about 1 volt.

The phrase "provide a redox potential range of less than about X volts" refers to the fact that when a substituent providing such a redox potential range is incorporated into a compound, the compound into which it is incorporated has an oxidation potential less than or equal to X volts, where X is a numeric value.

The phrase "rapidly removed" when used in reference to a solvent comprising the organic molecule that is to be attached to the group IV element refers to a solvent that is substantially or completely removed within about 1 hour, more preferably within about 20 minutes, still more preferably within about 10 minutes, and most preferably within about 5 minutes, 2 minutes or 1 minute under particular conditions (e.g. at a particular temperature, vacuum, etc.).

A "high boiling solvent" refers to a solvent having a boiling point greater than about 130° C., preferably greater than about 150° C., more preferably greater than about 180° C., and most preferably greater than about 200° C.).

DETAILED DESCRIPTION

This invention pertains to the design and fabrication of a novel architecture that can be used for a molecular electrochemical memory device, a sensor, and a variety of other applications. The unique architecture is comprised, in certain embodiments, of two or more arrays of conductors (e.g. electrodes) arranged so that the conductors forming the cross or overlap each other. The conductors are typically separated by a dialectric layer. Within each intersection point of an upper and lower electrode (e.g. top and bottom interconnect) a well is fabricated. This well penetrates the electrodes, so that the electrodes form a portion of the side and/or bottom of the well.

Molecules (e.g. organic molecules) are attached to one or more of the exposed conductor surfaces in the wells. Each well can then function as an electrochemical cell permitting electrochemical measurements of the bound molecules or of other molecules attached to the bound molecules.

The fabrication methods of this invention facilitate the production of single nano-scale wells or of arrays comprising hundreds, thousands, or millions of such wells (electrochemical cells), having precisely determined features (e.g. well volume, electrode surface area, etc.). These wells and well arrays are useful for the production of electrochemical memory devices, sensors, and the like. This fabrication approaches described herein convey numerous advantages as discussed below.

Molehole Array Design.

Architecture.

Figure 1:
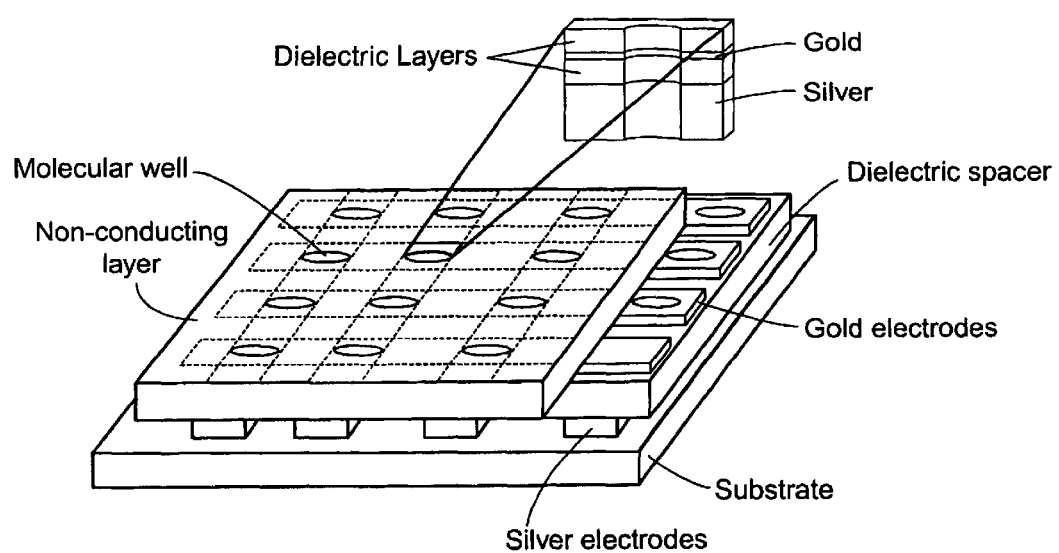
FIG. 1 illustrates one embodiment of a three-dimensional molehole array.

One preferred embodiment of a molehole array of this invention is illustrated in FIG. 1. As shown in this figure, the architecture comprises a series of conducting or semiconducting wires (e.g. fabricated metal, organic conductor, or semiconductor) stacked and separated in three dimensions using alternating insulating layers between each conducting wire. In particularly preferred embodiments, one or more species of molecule (preferably an organic molecule) is coupled to one or more conductors (electrodes) comprising a wall of the molehole.

In the illustrated embodiment, gold and silver are used to fabricate the alternating components of the conductor array. The first array of silver layers is fabricated directly on a substrate of interest, e.g. glass, thermally grown silicon oxide, a semiconductor, a plastic, a mineral, and the like. The insulator (e.g. dialectric) layer completely covers the silver conductor array. The gold array is deposited on top of the insulating spacer, either parallel to the silver array or at an angle to the silver array (e.g. perpendicular to the array). The gold array is then insulated by another non-conductor (e.g. another dialectric).

The wells are patterned at regions where the gold conductor array overlaps the silver conductor array and etched, e.g. using wet etching, reactive ion etching (RIE), or chemically assisted ion beam milling (CAIBM). Formation of the wells results in the creation of conductor (in this example gold and silver) rings in the walls and/or floor of the wells. The conductor regions in the walls are separated by one or more insulating layer(s). By varying the thickness of the conductor(s) and/or the insulator, the exposed area of each conductor and insulator can be precisely regulated (determined). In preferred embodiments, each well in the array is individually isolated from neighboring wells. A molecule (e.g. an organic molecule) can then be coupled to the surface of one or more conductors (electrodes) comprising each molehole.

Figure 2:
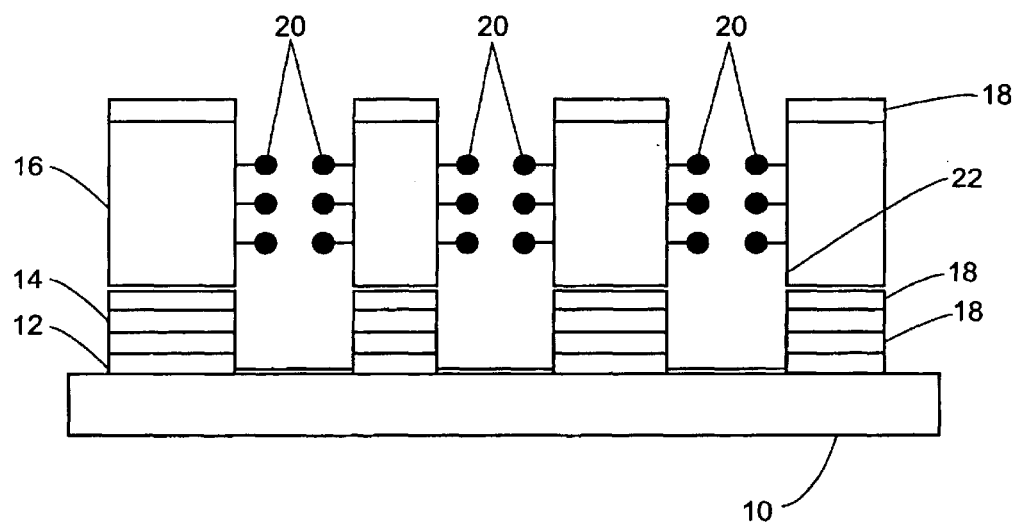
FIG. 2 illustrates a cross-section view of three moleholes from a molehole array.

A cross-section of three such wells is illustrated in FIG. 2. In the embodiment illustrate in this figure, a substrate 10 is coated with a first conductor 12, a second conductor 14, and a third conductor 16 with an insulating layer 18 between each conducting layer. In this figure three wells are shown etched through the conducting layers the insulating layers 18 and partially through conducting layer 12. This produces a well (molehole) having three different conducting surfaces. A bottom conducting surface (conductor 12) and two conducting surfaces (conductors 14 and 16) on the sides of the well. Organic molecules 20, e.g. a redox active molecule, a binding partner, etc., are shown attached to conductor 14 which can then be used as a working electrode for electrochemical measurements. Each well thus forms an electrochemical cell with a separate working electrode uniquely addressing each cell. Electrochemical measurements can readily be made on each individual cell or on combinations of cells. The third conductor 12 is optional, but, when present, can be conveniently used to bias a cell or combination of cells.

Figure 3:
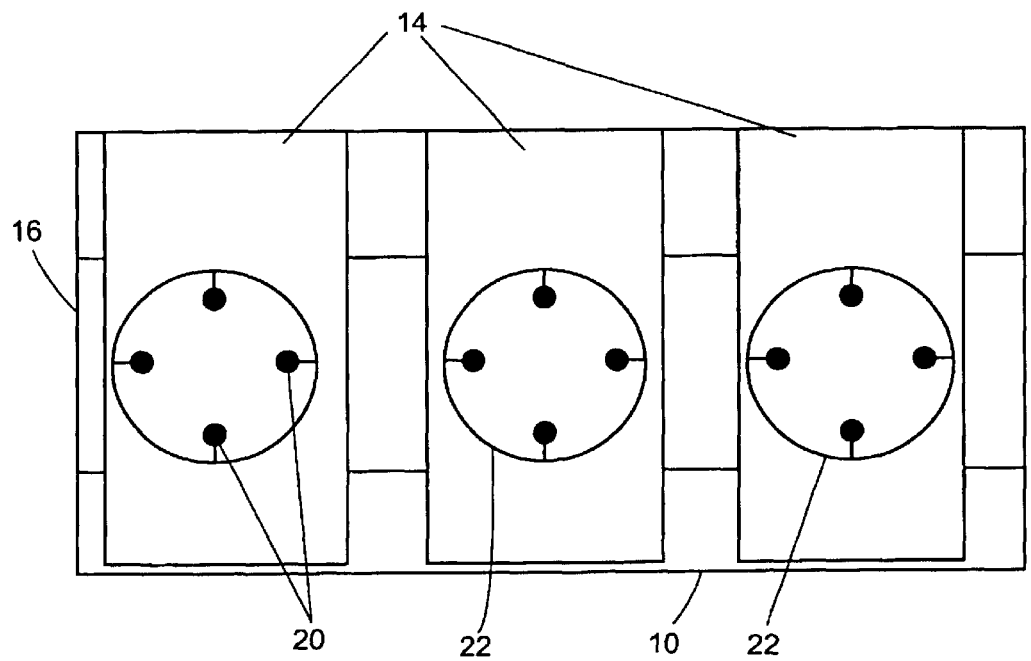
FIG. 3 illustrates a top-down view of three moleholes from a molehole array where all three moleholes share one common counter electrode 16 and each molehole has an individual working electrode 14.

FIG. 3 illustrates a top-down view of three moleholes. In this view it can be seen that the conductor (electrode) arrays, conductors 14 and 16, are deposited perpendicular to each other. In this case, each cell is addressed with a unique working electrode 14 and all three cells are addressed with a common counter electrode 16.

While the conductors 14 and 16 are illustrated in a perpendicular orientation with respect to each other, the various conductors or conductor arrays can be arranged at essentially any angle. Because each conductor is at a different level (e.g. position along the z-axis) in the architecture (see, e.g., FIG. 2) the conductors or conductor arrays can even be parallel and overlapping. Thus, for example, the cross-section shown in FIG. 2 could be looking along the long axis of both conductor 14 and conductor 16.

Figure 4:
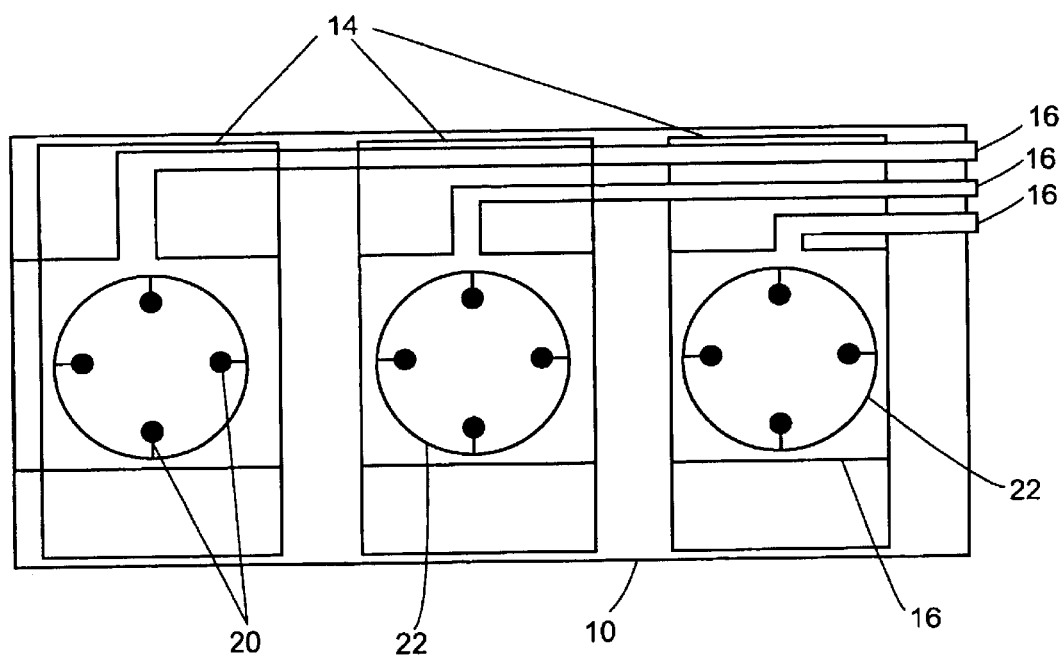
FIG. 4 illustrates a top-down view of three moleholes from a molehole array where each molehole has an individual counter electrode 16 and an individual each molehole has an individual working electrode 14.

FIG. 3 illustrates moleholes sharing a common conductor 16 and individual conductors 14. It is possible, in certain embodiments, for each cell to be uniquely addressed by every conductor contacting that cell. This embodiment is illustrated in FIG. 4 where each cell is addressed by a uniqe conductor 14 and a unique conductor 16. In a single molehole array, it is possible that certain cells are uniquely addressed by one or more conductors while other cells (e.g. groups of cells) share one or more common conductors.

The wells (moleholes) can be fabricated in essentially any shape. Such shapes include, but are not limited to regular polygons (e.g., circles, squares, octagons, etc) or any desired irregular shape.

In preferred embodiments, the wells have a cross-sectional area less than about 1 $\mu m^2$, more preferably less than about 100 nm by 100 nm, and most preferably by less than about 50 nm by 50 nm. The wells can be essentially any convenient depth. In preferred embodiments, the wells have a volume of about 100 femtoliters ($100 \times 10^{-15}$ L) or less, preferably about 10 femtoliters ($10 \times 10^{-15}$ L) or less, and most preferably about 1 femtoliter ($1 \times 10^{-15}$ L). In certain embodiments, there might be only a single well. Other embodiments, contemplate collections (e.g. arrays) of wells. Preferred arrays of wells comprise at least about 2 wells, preferably at least about 10 wells, more preferably at least about 100, 500, or 1,000 wells, and most preferably at least about 10,000, 100,000, or 1,000,000 wells.

Where the wells comprise a molecule (e.g. a redox-active species, a binding partner, etc.) attached to one or more conductors, in certain embodiments, each well comprises a different species of molecule. In other embodiments, multiple wells or even all of the wells comprise the same species of molecule. In certain embodiments, molehole arrays comprise at least one species of redox-active molecule or binding partner, more preferably at least two species, still more preferably at least five or ten species, and most preferably at least about 50, 100, 500, 1000, 10,000 different species.

Figure 5:
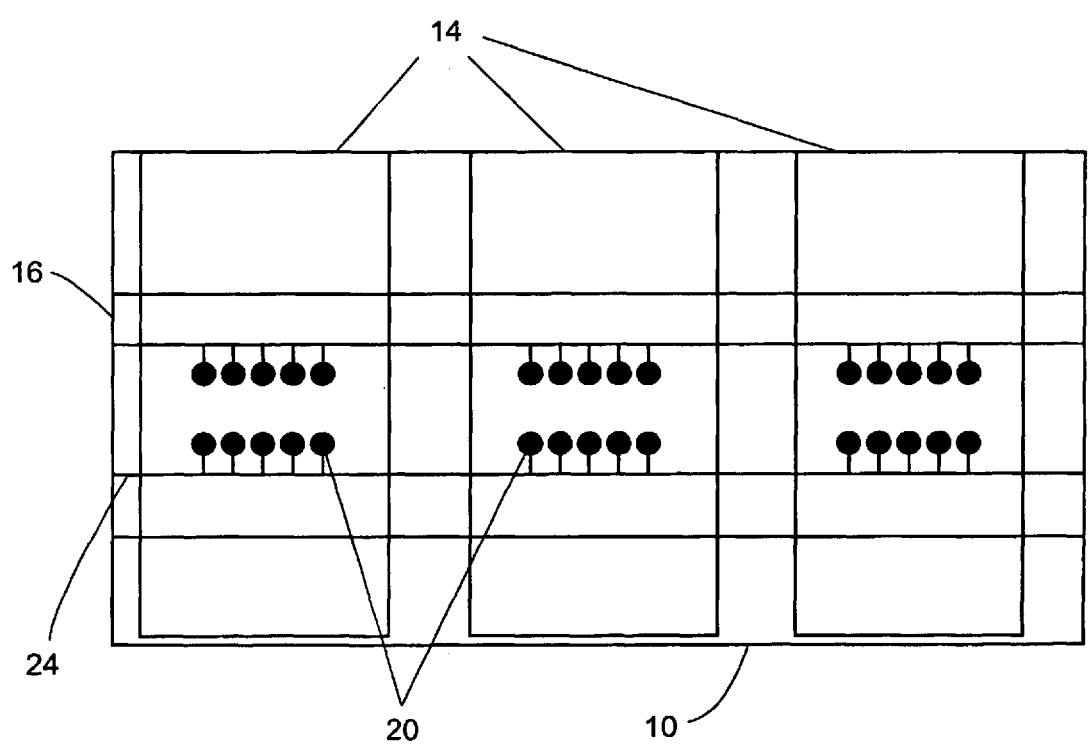
FIG. 5 illustrates a channel made according to this invention.

In certain embodiments, the moleholes are not limited to discrete wells. Other geometries are also available. Thus, in one preferred embodiment, the moleholes are actually fabricated as channels (see, e.g., FIG. 5). If the channel is aligned along the length of one or more conductors, the conductor provides an exposed surface all along the channel (see, e.g., conductor 16 in FIG. 5). Conversely, where the channel crosses a conductor, the conductor presents a surface at just that location. If the channel crosses a number of conductors, each conductor will present a surface at a discrete location along the channel (see, e.g., conductors 14 in FIG. 5).

Such channels are particularly useful in the manufacture of lab on a chip devices. In preferred embodiments of such devices a binding partner 14 (e.g. an antibody, a nucleic acid, a lectin, a receptor, etc.) is coupled to one or more electrodes comprising the walls of the channel. As analytes flow through the channel 24, particular analytes are captured by the binding partner(s) 14 and the captured analyte(s) can be electrochemically detected. Preferred channels have a width about 1 µm or less, more preferably about 100 nm or less, and most preferably about 50, 25, or 10 nm or less.

In preferred embodiments, the moleholes or channels of this invention are fabricated so that two conductors expose significantly different amounts of surface area to the interior of the molehole or channel. In a two electrode electrochemical cell, the electrode with the smallest area controls the reaction. By making the working electrode surface small relative to the counterelectrode, the electrochemical cell reaction is dominated by the electrochemical processes occurring at the surface of the working electrode. Thus, making the counter electrode surface area large relative to the working electrode, the signal to noise ratio of an electrochemical measurement is improved (i.e., the electrochemical performance of the cell is dominated by the electrochemical characteristics of the moieties attached to the working electrode). Typically the counter electrode has at least two times, preferably at least 5 times, more preferably at least 10 times, and most preferably at least 20 times, 50 times, or at least 100 times more surface area than the working electrode.

By using the thickness of the deposited conductor layers to determine electrode surface area, rather than using the tops, bottoms, or ends of wires, this invention permits extremely precise regulation of exposed electrode surface area. In addition, two electrodes having widely different exposed surface areas can be accommodated in an extremely small well. The electrode area is determined by the well diameter (for a round well) and the thickness of the deposited metal film, sizing the electrode to nanometer dimensions. For example, if the cylinder diameter and the thickness of the metal film were 1 nm and 100 nm, respectively, which can be achievable by photolithography and the vacuum evaporation, the electrode area would be about 314 $nm^2$.

In addition, this architecture avoids depositing metal directly onto the molecular layer, thereby preventing any damage to the monolayer which might become a significant problem in other proposed architectures.

The effective capacitance at each junction is diminished by the removal of a large area of dielectric spacer between the two metal electrodes at each intersection. This may have an effect on the overall metal wire capacitance; however, it should not impact the wire resistance significantly if the metal wire is thick enough.

In addition, the design enables for physical isolation of each electrochemical cell thereby preventing any cross-electric communication between neighboring cells.

Molehole Array Fabrication.

The moleholes and/or molehole arrays of this invention can be fabricated of any of a number of convenient and well-known materials. Suitable conductor materials include, but are not limited to consisting of copper, silver, tungsten, nickel, palladium, iron, tin, zinc, cadmium, indium, chromium, gold, platinum, aluminum, aluminum, silicon, germanium, gallium arsenide, ruthenium, titanium, tantalum, carbon nanotubes, carbon nanoribbons, a conducting polymer, and the like.

Conducting polymers include intrinsically conductive polymers (polymers that conduct electric currents without the addition of conductive (inorganic) substances) and doped conductive polymers. Conductive polymers are well known to those of skill in the art (see, e.g., (U.S. Pat. Nos. 5,096,586; 358,556; and *The Handbook of Conducting Polymers*, 2nd Edition, 945, 1997). One well known and commercially available intrinsically conducting polymer is Polyaniline (PAni) (ORMECON™)".

Semiconductors can also be used as the "conductors" in the moleholes and molehole arrays of this invention. Suitable semiconductors include, but are not limited to silicon, germanium, n- or p-doped silicon or germanium various doped carbon nanotubes or nanoribbon, and the like. Preferred semiconducting materials include, but are not limited to silicon, dense silicon carbide, boron carbide, $Fe_3O_4$, germanium, silicon germanium, silicon carbide, tungsten carbide, titanium carbide, indium phosphide, gallium nitride, gallium phosphide, aluminum phosphide, aluminum arsenide, mercury cadmium telluride, tellurium, selenium, ZnS, ZnO, ZnSe, CdS, ZnTe, GaSe, CdSe, CdTe, GaAs, InP, GaSb, InAs, Te, PbS, InSb, PbTe, PbSe, tungsten disulfide, and the like.

Insulating materials are also well known to those of skill in the art. Such materials include, but are not limited to high resistivity plastics, insulating oxides or sulfides of the transition metals in the periodic table of the elements, ceramics, glass, and the like. Examples of preferred insulators include chemical vapor deposition insulator materials (e.g. silicon nitride, silicon oxide, etc.), and spin-on insulator materials (e.g. spin-on glass). In various preferred embodiment, the insulator is a dialectric or includes a dialectric layer. Suitable dialetrics include, but are not limited to nafion, cellulose acetate, polystyrene sulfonate, poly(vinylpyridine), electronically conducting polymers such as polypyrrolic acid and polyaniline, etc.

The molehole architecture described herein is fabricated using standard methods well known in the electronics and micromaching industry. In a referred embodiment, the molehole architecture is fabricated using electron-beam vacuum deposition, photolithography, plasma enhanced chemical vapor deposition (PECVD), RIE and/or CAIBM techniques.

Figure 6:
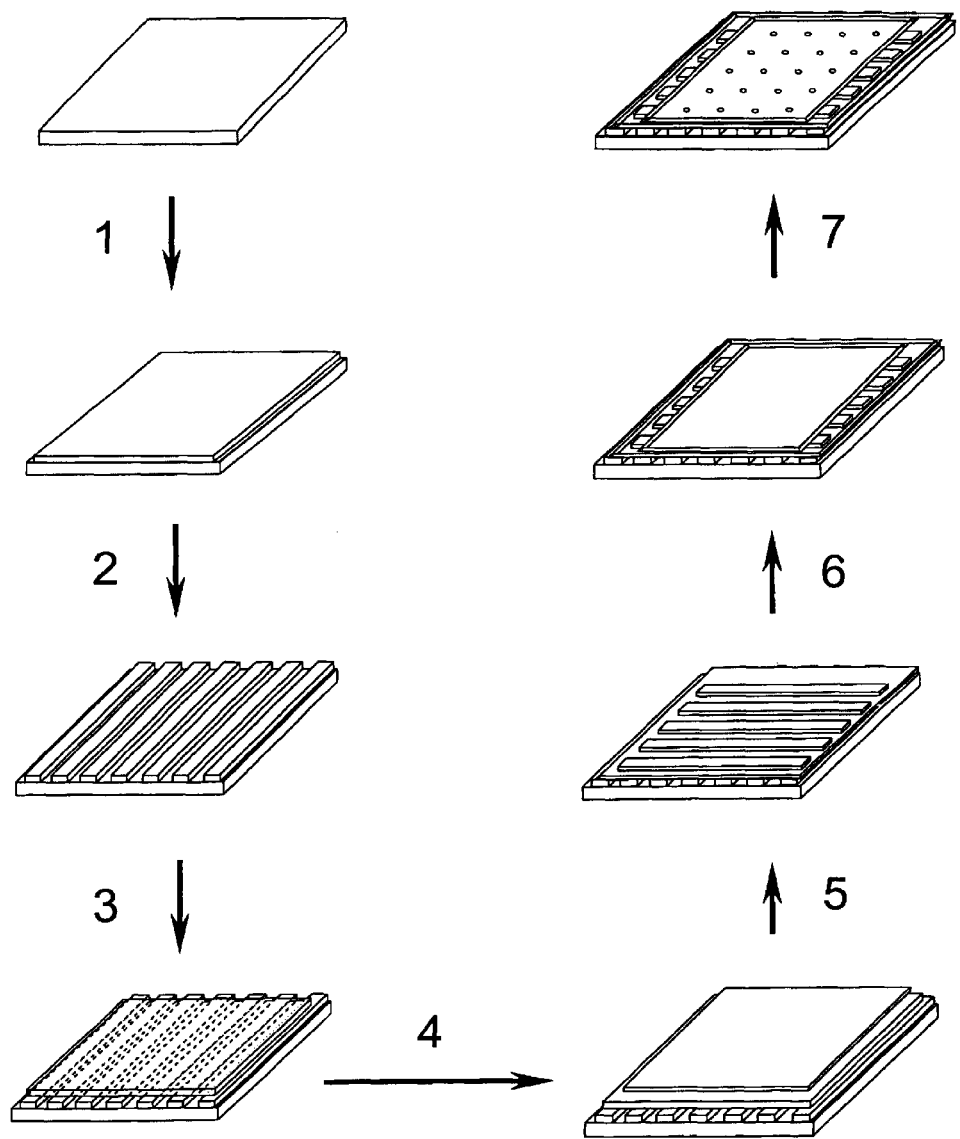
FIG. 6 illustrates a fabrication process for making a molecular well-embedded architecture of this invention.

One fabrication procedure is illustrated in FIG. 6. Substrates (e.g. glass, thermally oxidized silicon wafers, etc.) are cleaned using standard methods in the semiconductor industry (see, e.g., Choudhury (1997) *The Handbook of Microlithography, Micromachining, and Microfabrication*, Soc. Photo-Optical Instru. Engineer, Bard & Faulkner (1997) *Fundamentals of Microfabrication*, and the like). In one embodiment, the wafers are cleaned with a hot Piranha solution before use. Then a conducting film (e.g. a silver film) is deposited on the wafer surface, e.g. after the deposition of a thin chromium film using electron beam vacuum evaporation. A positive photoresist is spin-coated on the silver film. The resist film is exposed to UV light through a photomask using a contact mode mask aligner, is developed in a resist developer, and rinsed in deionized water. The silver film and chromium under-layer, uncovered by the photoresist pattern, are etched with silver and chromium etchants respectively. This is followed by the removal of photoresist pattern using a photoresist stripper. The resulting silver pattern consists of an array of silver lines with contact leads.

A dielectric layer is deposited on the silver pattern using plasma enhanced chemical vapor deposition (PECVD). A chromium under-layer and a gold film are deposited on the dielectric layer by electron beam vacuum evaporation. The gold array of lines is fabricated using the same photolithography and wet etching processes used for the silver layer. In one embodiment, the gold array is perpendicular to the silver array under the dielectric layer. A second dielectric layer is deposited on the top of the gold array by PECVD.

A photoresist pattern fabricated on the second dielectric layer exposes areas for the leads and a small hole on the top of each intersection. Using reactive ion etching (RIE) and chemically assisted ion beam milling (CAIBM) techniques, a well (e.g. a cylindrical well) is formed at each intersection by etching the dielectric and metallic layers completely down to the base substrate. The dielectric layers covering the leads are also removed.

This fabrication method is merely illustrative. Using the teaching provided herein, numerous other photolithographic and/or micromaching techniques can be used to fabricate individual moleholes or molehole arrays of this invention. The micromachining techniques described above, as well as many others, are well known to those of skill in the art (see, e.g., Choudhury (1997) *The Handbook of Microlithography, Micromachining, and Microfabrication*, Soc. Photo-Optical Instru. Engineer, Bard & Faulkner (1997) *Fundamentals of Microfabrication*). In addition, examples of the use of micromachining techniques on silicon or borosilicate glass chips can be found in U.S. Pat. Nos. 5,194,133, 5,132,012, 4,908,112, and 4,891,120.

Various molecules (e.g. redox-active molecules, binding partners, etc.) can be coupled to one or more electrodes in the well using standard methods well known to those of skill in the art. In preferred embodiments, the molecules are electrically coupled to the working electrode(s) in a cell.

The term "electrically coupled" is used to refer to coupling schemes that permit the attached molecule (e.g. redox-active molecule or binding partner) to gain or lose electrons to the electrode. The coupling can be a direct attachment of the molecule to the electrode, or an indirect attachment (e.g. via a linker). The attachment can be a covalent linkage, an ionic linkage, a linkage driven by hydrogen bonding or can involve no actual chemical attachment, but simply a juxtaposition of the electrode to the molecule. In some embodiments, the electrode can be some distance (e.g, about 5 Å to about 50 Å) from the molecule and electrical coupling can be via electron tunneling.

In some preferred embodiments, a "linker" is used to attach the molecule(s) to the electrode. The linker can be electrically conductive or it can be short enough that electrons can pass directly or indirectly between the electrode and a molecule of the storage medium.

The manner of linking a wide variety of compounds to various surfaces is well known and is amply illustrated in the literature. Means of coupling the molecules will be recognized by those of skill in the art. The linkage of the storage medium to a surface can be covalent, or by ionic or other non-covalent interactions. The surface and/or the molecule(s) may be specifically derivatized to provide convenient linking groups (e.g. sulfur, hydroxyl, amino, etc.).

The linker can be provided as a component of the molecule(s) or separately. Linkers, when not joined to the molecules to be linked are often either hetero- or homo-bifunctional molecules that contain two or more reactive sites that may each form a covalent bond with the respective binding partner (i.e. surface or redox-active molecule). When provided as a component of the molecule to be attached, or attached to a substrate surface, the linkers are preferably spacers having one or more reactive sites suitable for bonding to the respective surface or molecule.

Linkers suitable for joining molecules are well known to those of skill in the art and include, but are not limited to any of a variety of, a straight or branched chain carbon linker, or a heterocyclic carbon linker, amino acid or peptide linkers, and the like. Particularly preferred linkers include, but are not limited to 4,4'-diphenylethyne, 4,4'-diphenylbutadiyne, 4,4'-biphenyl, 1,4-phenylene, 4,4'-stilbene, 1,4-bicyclooctane, 4,4'-azobenzene, 4,4'-benzylideneaniline, and 4,4''-terphenyl. Linkers include molecules that join one or more molecules of the storage medium to the electrode(s).

In preferred embodiments, the molecules (e.g. redox-active molecules, binding partners, etc.) are used that self-assemble on the desired electrode. Thus, for example, where the working electrode is gold, molecules bearing thiol groups or bearing linkers having thiol groups will self-assemble on the gold surface. Where there is more than one gold electrode, the molecules can be drawn to the desired surface by placing an appropriate (e.g. attractive) charge on the electrode to which they are to be attached and/or placing a "repellant" charge on the electrode that is not to be so coupled.

Where the electrodes comprise a group IV element (e.g. silicon, germanium, etc.) the molecules are readily coupled to the surface if provided with either a thiol group or an alcohol or with a linker comprising a thiol group or an alcohol. One methods of coupling a molecule comprising an alcohol or a thiol to a group IV element involves halogenating the group IV element surface; providing a solution comprising the molecule to be coupled to the surface where the is alcohol terminated (e.g., terminated with an alcohol selected from the group consisting of a primary alcohol, a secondary alcohol, a tertiary alcohol, a benzyl alcohol, and an aryl alcohol) or thiol terminated (e.g., a primary thiol, a secondary thiol, a tertiary thiol, a benzyl thiol, an arylthiol, etc.) and present in a solvent and said alcohol-terminated organic molecule is in a solvent (e.g., mesitylene, durene, o-dichlorobenzene, 1,2,4,-trichlorobenzene, 1-chloronaphthalene, 2-chloronaphthalene, N,N-dimethylformamide, N,N-dimethylacetamide, N,N-dimethylpropionamide, benzonitrile, anisole, etc.); and contacting the solution with the group IV element surface under conditions where the solvent is rapidly removed from the surface whereby the organic molecule is coupled to said surface through an E—O- or an E—S-bond where E is the group IV element (e.g. silicon, germanium, doped silicon, doped germanium, etc.). The reaction is preferably performed in the presence of a base (e.g. 2,4,6-collidine, 2,6-lutidine, 2,6-di-tert-butylpyridine, 4-dimethylaminopyridine, trimethylamine, triethylamine, tributylamine, N,N-diisopropylethylamine, 1,8-bis (dimethylamino)naphthalene, 1,5-diazabicyclo[4.3.0]non-5-ene, 1,8-diazabicyclo[5.4.0]undec-7-ene, $Na_2CO_3$, $NH_3$. etc.). Typically the surface is heated to a temperature of at least about 70° C.

Using the teachings provided herein, other methods of coupling a molecule to one or more electrodes comprising the molehole or molehole array will be routinely implemented by one of skill in the art.

Uses of Moleholes and Molehole Arrays.

The multielectrode arrays described herein (molehole arrays) can be used as an integrated memory component in a molecular based electronic device. In addition, the nano-wells can be used as nano-electrodes to measure the rates of electron transfer of electroactive molecular monolayers or as molecular switches by suspending a single bound electroactive molecule in a single well.

The multi-integrated molecular well also finds bioanalytical applications. This architecture is suitable for derivatization and sensing of proteins, DNA, and single cell analysis using electrochemical detection or fluorescence. Such electrochemical cell arrays are well suitable for high-throughput analysis schemes using numerous electroactive analytes or non-electroactive analytes through indirect detection schemes. The design is easily integrated with existing on chip microfluidic systems.

Molehole-Based Memory Elements.

The multi-electrode molehole arrays of this invention are well suited for use as memory elements in molecular based electronic devices. In "molecular memory" elements redox-active molecules (molecules having one or more non-zero redox states) coupled to an electrode (e.g. the working electrode) in a molehole are used to store bits (e.g. in certain embodiments, each redox state can represent a bit or a combination of bits). The redox-active molecule attached to the electrode (e.g. silicon or germanium) forms a storage cell capable of storing one or more bits in various oxidation states. In certain embodiments, the storage cell is characterized by a fixed working electrode electrically coupled to a "storage medium" comprising one or more redox-active molecules and having a multiplicity of different and distinguishable oxidation states. Data is stored in the (preferably non-neutral) oxidation states by the addition or withdrawal of one or more electrons from said storage medium via the electrically coupled electrode. The oxidation state of the redox-active molecule(s) can be set and/or read using electrochemical methods (e.g. cyclic voltammetry), e.g., as described in U.S. Pat. Nos. 6,272,038, 6,212,093, and 6,208,553 and PCT Publication WO 01/03126. A molehole array comprising a plurality of moleholes (electrochemical cells) can provide a high capacity, high density memory device.

Because group IV elements, in particular silicon and germanium, are commonly used in electronic chip fabrication, the methods provided herein readily lend themselves to the fabrication of molecular memory chips compatible with existing processing/fabrication technologies. In addition, details on the construction and use of storage cells comprising redox-active molecules can be found, in U.S. Pat. Nos. 6,272,038, 6,212,093, and 6,208,553 and PCT Publication WO 01/03126.

Certain preferred redox-active molecules suitable for use in this invention are characterized by having a multiplicity of oxidation states. Those oxidation states are provided by one or more redox-active units. A redox-active unit refers to a molecule or to a subunit of a molecule that has one or more discrete oxidation states that can be set by application of an appropriate voltage. Thus, for example, in one embodiment, the redox-active molecule can comprise two or more (e.g. 8) different and distinguishable oxidation states. Typically, but not necessarily, such multi-state molecules will be composed of several redox-active units (e.g. porphyrins or ferrocenes). Each redox-active molecule is itself at least one redox-active unit, or comprises at least one redox-active unit, but can easily comprise two or more redox-active units.

Preferred redox-active molecules include, but are not limited to porphyrinic macrocycles. The term "porphyrinic macrocycle" refers to a porphyrin or porphyrin derivative. Such derivatives include porphyrins with extra rings ortho-fused, or ortho-perifused, to the porphyrin nucleus, porphyrins having a replacement of one or more carbon atoms of the porphyrin ring by an atom of another element (skeletal replacement), derivatives having a replacement of a nitrogen atom of the porphyrin ring by an atom of another element (skeletal replacement of nitrogen), derivatives having substituents other than hydrogen located at the peripheral (meso-, β-) or core atoms of the porphyrin, derivatives with saturation of one or more bonds of the porphyrin (hydroporphyrins, e.g., chlorins, bacteriochlorins, isobacteriochlorins, decahydroporphyrins, corphins, pyrrocorphins, etc.), derivatives obtained by coordination of one or more metals to one or more porphyrin atoms (metalloporphyrins), derivatives having one or more atoms, including pyrrolic and pyrromethenyl units, inserted in the porphyrin ring (expanded porphyrins), derivatives having one or more groups removed from the porphyrin ring (contracted porphyrins, e.g., corrin, corrole) and combinations of the foregoing derivatives (e.g. phthalocyanines, sub-phthalocyanines, and porphyrin isomers). Preferred porphyrinic macrocycles comprise at least one 5-membered ring.

The term "porphyrin" refers to a cyclic structure typically composed of four pyrrole rings together with four nitrogen atoms and two replaceable hydrogens for which various metal atoms can readily be substituted. A typical porphyrin is hemin.

Particularly preferred redox-active molecules include a porphyrin, an expanded porphyrin, a contracted porphyrin, a ferrocene, a linear porphyrin polymer, a porphyrin sandwich coordination complex, and a porphyrin array.

In one preferred embodiment, the redox-active molecule is a metallocene as shown in Formula I.

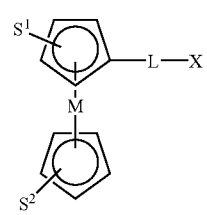

I where L is a linker, M is a metal (e.g., Fe, Ru, Os, Co, Ni, Ti, Nb, Mn, Re, V, Cr, W), $S^1$ and $S^2$ are substituents independently selected from the group consisting of aryl, phenyl, cycloalkyl, alkyl, halogen, alkoxy, alkylthio, perfluoroalkyl, perfluoroaryl, pyridyl, cyano, thiocyanato, nitro, amino, alkylamino, acyl, sulfoxyl, sulfonyl, imido, amido, and carbamoyl. In preferred embodiments, a substituted aryl group is attached to the porphyrin, and the substituents on the aryl group are selected from the group consisting of aryl, phenyl, cycloalkyl, alkyl, halogen, alkoxy, alkylthio, perfluoroalkyl, perfluoroaryl, pyridyl, cyano, thiocyanato, nitro, amino, alkylamino, acyl, sulfoxyl, sulfonyl, imido, amido, and carbamoyl.

Particularly preferred substituents include, but are not limited to, 4-chlorophenyl, 3-acetamidophenyl, 2,4-dichloro-4-trifluoromethyl. Preferred substituents provide a redox potential range of less than about 2 volts. X is selected from the group consisting of a substrate, a reactive site that can covalently couple to a substrate (e.g. an alcohol, a thiol, etc.). It will be appreciated that in some embodiments, L-X is an alcohol or a thiol. In certain instances L-X can be replaced with another substituent (S3) like S1 or S2. In certain embodiments, L-X can be present or absent, and when present preferably is 4-hydroxyphenyl, 4-(2-(4-hydroxyphenyl)ethynyl)phenyl, 4-(hydroxymethyl)phenyl, 4-mercaptophenyl, 4-(2-(4-mercaptophenyl)ethynyl)phenyl, 4-(mercaptomethyl)phenyl, 4-hydroselenophenyl, 4-(2-(4-hydroselenophenyl)ethynyl)phenyl, 4-(hydroselenylmethyl)phenyl, 4-hydrotellurophenyl, 4-(2-(4-hydrotellurophenyl)ethynyl)phenyl, and 4-(hydrotelluromethyl)phenyl.

The oxidation state of molecules of Formula I is determined by the metal and the substituents. Thus, particular preferred embodiments are illustrated by Formulas II–VII, (listed sequentially) below:

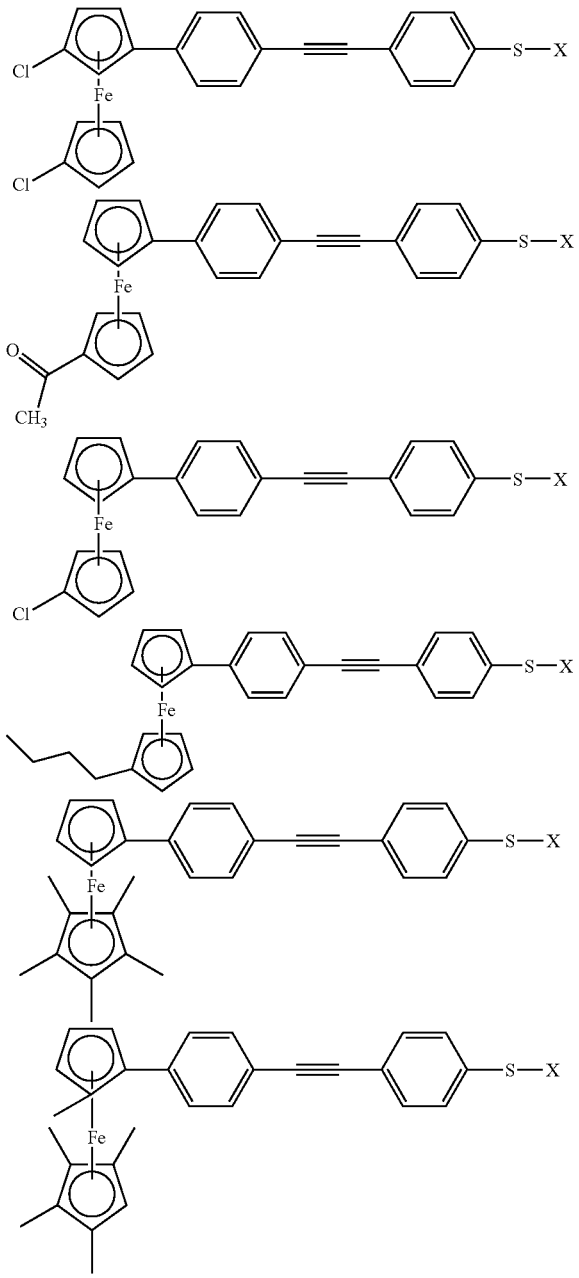

The ferrocenes listed above in Formulas II through VII provide a convenient series of one-bit molecules having different and distinguishable oxidation states. Thus the molecules of Formulas II through VII have oxidation states ($E_{1/2}$) of +0.55 V, +0.48V, +0.39 V, +0.17 V, −0.05 V, and −0.18 V, respectively, and provide a convenient series of molecules for incorporation into a storage medium of this invention. It will be appreciated that the oxidation potentials of the members of the series can be routinely altered by changing the metal (M) or the substituents.

Another preferred redox-active molecule is a porphyrin illustrated by Formula VIII.

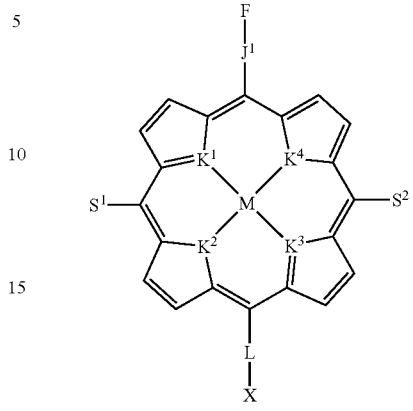

VIII where, F is a redox-active subunit (e.g., a ferrocene, a substituted ferrocene, a metalloporphyrin, or a metallochlorin, etc.), $J^1$ is a linker, M is a metal (e.g., Zn, Mg, Cd, Hg, Cu, Ag, Au, Ni, Pd, Pt, Co, Rh, Ir, Mn, B, Al, Ga, Pb, and Sn), $S^1$ and $S^2$ are independently selected from the group consisting of aryl, phenyl, cycloalkyl, alkyl, halogen, alkoxy, alkylthio, perfluoroalkyl, perfluoroaryl, pyridyl, cyano, thiocyanato, nitro, amino, alkylamino, acyl, sulfoxyl, sulfonyl, imido, amido, and carbamoyl wherein said substituents provide a redox potential range of less than about 2 volts, $K^1$, $K^2$, $K^3$, and $K^4$ are independently selected from the group consisting of N, O, S, Se, Te, and CH; L is a linker; X is selected from the group consisting of a substrate, a reactive site that can covalently couple to a substrate, and a reactive site that can ionically couple to a substrate. In preferred embodiments, X or L-X is an alcohol or a thiol. In some embodiments L-X can be eliminated and replaced with a substituent independently selected from the same group as $S^1$ or $S^2$.

Control over the hole-storage and hole-hopping properties of the redox-active units of the redox-active molecules used in the memory devices of this invention allows fine control over the architecture of the memory device.

Such control is exercised through synthetic design. The hole-storage properties depend on the oxidation potential of the redox-active units or subunits that are themselves or are that are used to assemble the storage media used in the devices of this invention. The hole-storage properties and redox potential can be tuned with precision by choice of base molecule(s), associated metals and peripheral substituents (Yang et al. (1999) *J. Porphyrins Phthalocyanines*, 3: 117–147).

For example, in the case of porphyrins, Mg porphyrins are more easily oxidized than Zn porphyrins, and electron withdrawing or electron releasing aryl groups can modulate the oxidation properties in predictable ways. Hole-hopping occurs among isoenergetic porphyrins in a nanostructure and is mediated via the covalent linker joining the porphyrins (Seth et al. (1994) *J. Am. Chem. Soc.*, 116: 10578–10592, Seth et al (1996) *J. Am. Chem. Soc.*, 118: 11194–11207, Strachan et al. (1997) *J. Am. Chem. Soc.*, 119: 11191–11201; Li et al. (1997) *J. Mater. Chem.*, 7: 1245–1262, Strachan et al. (1998) *Inorg. Chem.*, 37: 1191–1201, Yang et al. (1999) *J. Am. Chem. Soc.*, 121: 4008–4018).

The design of compounds with predicted redox potentials is well known to those of ordinary skill in the art. In general, the oxidation potentials of redox-active units or subunits are well known to those of skill in the art and can be looked up (see, e.g., *Handbook of Electrochemistry of the Elements*). Moreover, in general, the effects of various substituents on the redox potentials of a molecule are generally additive. Thus, a theoretical oxidation potential can be readily predicted for any potential data storage molecule. The actual oxidation potential, particularly the oxidation potential of the information storage molecule(s) or the information storage medium can be measured according to standard methods. Typically the oxidation potential is predicted by comparison of the experimentally determined oxidation potential of a base molecule and that of a base molecule bearing one substituent in order to determine the shift in potential due to that particular substituent. The sum of such substituent-dependent potential shifts for the respective substituents then gives the predicted oxidation potential.

Various preferred redox-active molecules and the syntheses thereof are described in detail in U.S. Pat. Nos. 6,272,038, 6,212,093, and 6,208,553 and PCT Publication WO 01/03126.

Sensor/Assay Applications.

The multi-electrode moleholes or molehole arrays of this invention are also well suited as components of sensors, e.g., in various bioanalytical applications. This architecture is suitable for derivatization and sensing of virtually any analyte including but not limited to proteins, DNA, sugars, carbohydrates, cells, and the like. The electrochemical cell arrays are particularly well suited for high-throughput analysis schemes using numerous electroactive analytes or non-electroactive analytes through indirect detection schemes. The design is easily integrated with existing on chip microfluidic systems.

In such embodiments, the molecule attached to the working electrode is preferably a binding partner. As used herein, the term "binding partner" or a member of a "binding pair" refers to a molecule or composition that specifically binds other molecules to form a binding complex such as antibody-antigen, lectin-carbohydrate, nucleic acid-nucleic acid, biotin-avidin, etc. Thus, particularly preferred binding partners include, but are not limited to antibodies, nucleic acids, proteins, lectins, receptors, and the like.

The binding partner, when coupled to an electrode in a molehole or a channel according to the methods of this invention can be used to capture (bind) and thereby immobilize a target analyte. The presence of the bound analyte can then be detected by any of a wide variety of means. For example, particularly where the binding partner is electrically coupled to the electrode, binding of a target analyte can be detected using electrochemical methods (e.g. cyclic/sinusoidal voltammetry, impedance spectrometry, coulometry, etc.).

The detection of bound target analytes using electrochemical methods is described in detail in U.S. Pat. Nos. 5,650,061, 5,958,215, and 6,294,392.

Other approaches can be used to detect the bound target analyte. Such approaches include, but are not limited to competitive assay formats, where the bound target analyte(s) displace a previously bound target (e.g. labeled target) and the amount of released target is measured and provides an indication of the presence or quantity of target analytes. Other assay formats include, but are not limited to sandwich assays in which the target analyte, after binding to the binding partner is then itself bound by a second molecule (e.g. an antibody specific for all or a part of the target analyte). The bound second molecule is then detected and provides a measure of the bound analyte. These assay formats are merely illustrative and not intended to be limiting. Using the teaching provided herein, other assay formats can readily be developed by one of skill in the art.

A single species of binding partner in each molehole (well). Alternatively, a plurality of binding partners can be attached in each molehole. Similarly, all of the moleholes comprising a binding partner in a molehole array can comprise the same species of binding partner, or different moleholes can comprise different biding partners. Certain preferred molehole arrays comprise at least 2, preferably at least 5, more preferably at least 10, and most preferably at least 20, 50, 100, or 1,000 different binding partners. Where a plurality of binding partners are used, the sensor formed thereby can detect a number of different analytes. Such multi-analyte sensors are particularly well suited to complex analyses, or to various high-throughput screening systems.

The molehole, or molehole array, can be fabricated as a vessel or component of a vessel or surface to which a sample is applied. The molehole, or molehole array can also be a fixed component of an integrated detection and analysis system or as a removable "cassette".

The moleholes, or molehole arrays, or channels or channel arrays of this invention are particularly well suited to incorporating organic molecules (e.g. binding partners) into "chip-based" formats for rapid screening. Various "lab on a chip" formats are well known to those of skill in the art (see, e.g., U.S. Pat. Nos. 6,132,685, 6,123,798, 6,107,044, 6,100,541, 6,090,251, 6,086,825, 6,086,740, 6,074,725, 6,071,478, 6,068,752, 6,048,498, 6,046,056, 6,042,710, and 6,042,709) and may readily be adapted for use with the methods of this invention.

Preferred binding partners specifically bind to the target analyte(s). The term "specifically binds", as used herein, when referring to a binding partner (e.g., protein, nucleic acid, antibody, etc.), refers to a binding reaction that is determinative of the presence of a target analyte in a heterogeneous population of molecules (e.g. proteins and other biologics). Thus, under designated conditions (e.g. immunoassay conditions in the case of an antibody, or stringent hybridization conditions in the case of a nucleic acid), the specified ligand or antibody binds to its particular "target" (e.g. a protein or nucleic acid) and does not bind in a significant amount to other molecules.

The binding partner(s) used in this invention are selected based upon the targets that are to be identified/quantified. Thus, for example, where the target is a nucleic acid the binding partner is preferably a nucleic acid or a nucleic acid binding protein. Where the target is a protein, the binding partner is preferably a receptor, a ligand, or an antibody that specifically binds that protein. Where the target is a sugar or glycoprotein, the binding partner is preferably a lectin, and so forth.

Suitable binding partners (capture agents) include, but are not limited to nucleic acids, proteins, receptor binding proteins, nucleic acid binding proteins, lectins, sugars, glycoproteins, antibodies, lipids, and the like. Methods of synthesizing or isolating such binding partners are well known to those of skill in the art. The binding partners can be readily derivatized to bear a thiol or an alcohol according to standard methods known to those of skill in the art. It is noted that where the binding partner is an antibody or a protein, cysteines, where present, will provide conveniently available thiol groups.

Preparation of Binding Partners (Capture Agents).

Nucleic Acids.

Nucleic acids for use as binding partners in this invention can be produced or isolated according to any of a number of methods well known to those of skill in the art. In one embodiment, the nucleic acid can be an isolated naturally occurring nucleic acid (e.g., genomic DNA, cDNA, mRNA, etc.). Methods of isolating naturally occurring nucleic acids are well known to those of skill in the art (see, e.g., Sambrook et al. (1989) *Molecular Cloning-A Laboratory Manual* (2nd Ed.), Vol. 1–3, Cold Spring Harbor Laboratory, Cold Spring Harbor, N.Y.).

However, in a preferred embodiment, the nucleic acid is created de novo, e.g. through chemical synthesis. In a preferred embodiment, nucleic acids (e.g., oligonucleotides) are chemically synthesized according to the solid phase phosphoramidite triester method described by Beaucage and Caruthers (1981), *Tetrahedron Letts*., 22(20): 1859–1862, e.g., using an automated synthesizer, as described in Needham-VanDevanter et al. (1984) *Nucleic Acids Res*., 12: 6159–6168. Purification of oligonucleotides, where necessary, is typically performed by either native acrylamide gel electrophoresis or by anion-exchange HPLC as described in Pearson and Regnier (1983) *J. Chrom*. 255: 137–149. The sequence of the synthetic oligonucleotides can be verified using the chemical degradation method of Maxam and Gilbert (1980) in Grossman and Moldave (eds.) Academic Press, New York, *Meth. Enzymol*. 65: 499–560.

Antibodies/Antibody Fragments.

Antibodies or antibody fragments for use as binding partners (capture agents) can be produced by a number of methods well known to those of skill in the art (see, e.g., Harlow & Lane (1988) *Antibodies: A Laboratory Manual*, Cold Spring Harbor Laboratory, and Asai (1993) *Methods in Cell Biology Vol*. 37: *Antibodies in Cell Biology*, Academic Press, Inc. N.Y.). In one approach, the antibodies are produced by immunizing an animal (e.g. a rabbit) with an immunogen containing the epitope it is desired to recognize/ capture. A number of immunogens may be used to produce specifically reactive antibodies. Recombinant protein is the preferred immunogen for the production of monoclonal or polyclonal antibodies. Naturally occurring protein may also be used either in pure or impure form. Synthetic peptides made as well using standard peptide synthesis chemistry (see, e.g., Barany and Merrifield, *Solid-Phase Peptide Synthesis*; pp. 3–284 in *The Peptides: Analysis, Synthesis, Biology. Vol. 2: Special Methods in Peptide Synthesis, Part A.*, Merrifield et al. (1963) *J. Am. Chem. Soc*., 85: 2149–2156, and Stewart et al. (1984) *Solid Phase Peptide Synthesis*, 2nd ed. Pierce Chem. Co., Rockford, Ill.)

Methods of production of polyclonal antibodies are known to those of skill in the art. In brief, an immunogen, preferably a purified cytoskeletal component, is mixed with an adjuvant and animals are immunized. The animal's immune response to the immunogen preparation is monitored by taking test bleeds and determining the titer of reactivity to the cytoskeletal components and test compositions. When appropriately high titers of antibody to the immunogen are obtained, blood is collected from the animal and antisera are prepared. Further fractionation of the antisera to enrich for antibodies reactive to the cytoskeletal component can be done if desired. (See Harlow and Lane, supra).

Monoclonal antibodies may be obtained by various techniques familiar to those skilled in the art. Briefly, spleen cells from an animal immunized with a desired antigen are immortalized, commonly by fusion with a myeloma cell (See, Kohler and Milstein (1976) *Eur. J. Immunol*. 6: 511–519). Alternative methods of immortalization include transformation with Epstein Barr Virus, oncogenes, or retroviruses, or other methods well known in the art. Colonies arising from single immortalized cells are screened for production of antibodies of the desired specificity and affinity for the antigen, and yield of the monoclonal antibodies produced by such cells may be enhanced by various techniques, including injection into the peritoneal cavity of a vertebrate host. Alternatively, one may isolate DNA sequences which encode a monoclonal antibody or a binding fragment thereof by screening a DNA library from human B cells according to the general protocol outlined by Huse et al. (1989) *Science*, 246:1275–1281.

Antibodies fragments, e.g. single chain antibodies (scFv or others), can also be produced/selected using phage display technology. The ability to express antibody fragments on the surface of viruses that infect bacteria (bacteriophage or phage) makes it possible to isolate a single binding antibody fragment from a library of greater than $10^{10}$ nonbinding clones. To express antibody fragments on the surface of phage (phage display), an antibody fragment gene is inserted into the gene encoding a phage surface protein (pIII) and the antibody fragment-pIII fusion protein is displayed on the phage surface (McCafferty et al. (1990) *Nature*, 348: 552–554; Hoogenboom et al. (1991) *Nucleic Acids Res*. 19: 4133–4137).

Since the antibody fragments on the surface of the phage are functional, phage bearing antigen binding antibody fragments can be separated from non-binding phage by antigen affinity chromatography (McCafferty et al. (1990) *Nature*, 348: 552–554). Depending on the affinity of the antibody fragment, enrichment factors of 20 fold-1,000,000 fold are obtained for a single round of affinity selection. By infecting bacteria with the eluted phage, however, more phage can be grown and subjected to another round of selection. In this way, an enrichment of 1000 fold in one round can become 1,000,000 fold in two rounds of selection (McCafferty et al. (1990) *Nature*, 348: 552–554). Thus even when enrichments are low (Marks et al. (1991) *J. Mol. Biol*. 222: 581–597), multiple rounds of affinity selection can lead to the isolation of rare phage. Since selection of the phage antibody library on antigen results in enrichment, the majority of clones bind antigen after as few as three to four rounds of selection. Thus only a relatively small number of clones (several hundred) need to be analyzed for binding to antigen.

Human antibodies can be produced without prior immunization by displaying very large and diverse V-gene repertoires on phage (Marks et al. (1991) *J. Mol. Biol*. 222: 581–597). In one embodiment natural $V_H$ and $V_L$ repertoires present in human peripheral blood lymphocytes are were isolated from unimmunized donors by PCR. The V-gene repertoires were spliced together at random using PCR to create a scFv gene repertoire which is was cloned into a phage vector to create a library of 30 million phage antibodies (Id.). From this single "naive" phage antibody library, binding antibody fragments have been isolated against more than 17 different antigens, including haptens, polysaccharides and proteins (Marks et al. (1991) *J. Mol. Biol*. 222: 581–597; Marks et al. (1993). *Bio/Technology*. 10: 779–783; Griffiths et al. (1993) *EMBO J*. 12: 725–734; Clackson et al. (1991) *Nature*. 352: 624–628). Antibodies have been produced against self proteins, including human thyroglobulin, immunoglobulin, tumor necrosis factor and CEA (Griffiths et al. (1993) *EMBO J*. 12: 725–734). It is also possible to isolate antibodies against cell surface antigens by selecting directly on intact cells. The antibody fragments are highly specific for the antigen used for selection and have affinities in the 1 :M to 100 nM range (Marks et al. (1991) *J. Mol. Biol*. 222: 581–597; Griffiths et al. (1993) *EMBO J*. 12: 725–734). Larger phage antibody libraries result in the isolation of more antibodies of higher binding affinity to a greater proportion of antigens.

Binding Proteins.

In one embodiment, the binding partner (capture agent) can be a binding protein. Suitable binding proteins include, but are not limited to receptors (e.g. cell surface receptors), receptor ligands, cytokines, transcription factors and other nucleic acid binding proteins, growth factors, etc.

The protein can be isolated from natural sources, mutagenized from isolated proteins or synthesized de novo. Means of isolating naturally occurring proteins are well known to those of skill in the art. Such methods include but are not limited to well known protein purification methods including ammonium sulfate precipitation, affinity columns, column chromatography, gel electrophoresis and the like (see, generally, R. Scopes, (1982) *Protein Purification*, Springer-Verlag, N.Y.; Deutscher (1990) *Methods in Enzymology Vol. 182: Guide to Protein Purification*, Academic Press, Inc. N.Y.).

Where the protein binds a target reversibly, affinity columns bearing the target can be used to affinity purify the protein. Alternatively the protein can be recombinantly expressed with a HIS-Tag and purified using $Ni^{2+}$/NTA chromatography.

In another embodiment, the protein can be chemically synthesized using standard chemical peptide synthesis techniques. Where the desired subsequences are relatively short the molecule may be synthesized as a single contiguous polypeptide. Where larger molecules are desired, subsequences can be synthesized separately (in one or more units) and then fused by condensation of the amino terminus of one molecule with the carboxyl terminus of the other molecule thereby forming a peptide bond. This is typically accomplished using the same chemistry (e.g., Fmoc, Tboc) used to couple single amino acids in commercial peptide synthesizers.

Solid phase synthesis in which the C-terminal amino acid of the sequence is attached to an insoluble support followed by sequential addition of the remaining amino acids in the sequence is the preferred method for the chemical synthesis of the polypeptides of this invention. Techniques for solid phase synthesis are described by Barany and Merrifield (1962) *Solid-Phase Peptide Synthesis*; pp. 3–284 in *The Peptides: Analysis, Synthesis, Biology. Vol. 2: Special Methods in Peptide Synthesis, Part A.*, Merrifield et al. (1963) *J. Am. Chem. Soc.*, 85: 2149–2156, and Stewart et al. (1984) *Solid Phase Peptide Synthesis*, 2nd ed. Pierce Chem. Co., Rockford, Ill.

In a preferred embodiment, the can also be synthesized using recombinant DNA methodology. Generally this involves creating a DNA sequence that encodes the binding protein, placing the DNA in an expression cassette under the control of a particular promoter, expressing the protein in a host, isolating the expressed protein and, if required, renaturing the protein.

DNA encoding binding proteins or subsequences of this invention can be prepared by any suitable method as described above, including, for example, cloning and restriction of appropriate sequences or direct chemical synthesis by methods such as the phosphotriester method of Narang et al. (1979) *Meth. Enzymol.* 68: 90–99; the phosphodiester method of Brown et al. (1979) *Meth. Enzymol.* 68: 109–151; the diethylphosphoramidite method of Beaucage et al. (1981) *Tetra. Lett.*, 22: 1859–1862; and the solid support method of U.S. Pat. No. 4,458,066.

The nucleic acid sequences encoding the desired binding protein(s) may be expressed in a variety of host cells, including *E. coli*, other bacterial hosts, yeast, and various higher eukaryotic cells such as the COS, CHO and HeLa cells lines and myeloma cell lines. The recombinant protein gene will be operably linked to appropriate expression control sequences for each host. For *E. coli* this includes a promoter such as the T7, trp, or lambda promoters, a ribosome binding site and preferably a transcription termination signal. For eukaryotic cells, the control sequences will include a promoter and preferably an enhancer derived from immunoglobulin genes, SV40, cytomegalovirus, etc., and a polyadenylation sequence, and may include splice donor and acceptor sequences.

The plasmids can be transferred into the chosen host cell by well-known methods such as calcium chloride transformation for *E. coli* and calcium phosphate treatment or electroporation for mammalian cells. Cells transformed by the plasmids can be selected by resistance to antibiotics conferred by genes contained on the plasmids, such as the amp, gpt, neo and hyg genes.

Once expressed, the recombinant binding proteins can be purified according to standard procedures of the art as described above.

Sugars and Carbohydrates.

Other binding partners include sugars and carbohydrates. Sugars and carbohydrates can be isolated from natural sources, enzymatically synthesized or chemically synthesized. A route to production of specific oligosaccharide structures is through the use of the enzymes which make them in vivo; the glycosyltransferases. Such enzymes can be used as regio- and stereoselective catalysts for the in vitro synthesis of oligosaccharides (Ichikawa et al. (1992) *Anal. Biochem.* 202: 215–238). Sialyltransferase can be used in combination with additional glycosyltransferases. For example, one can use a combination of sialyltransferase and galactosyltransferases. A number of methods of using glycosyltransferases to synthesize desired oligosaccharide structures are known. Exemplary methods are described, for instance, WO 96/32491, Ito et al. (1993) *Pure Appl. Chem.* 65:753, and U.S. Pat. Nos. 5,352,670, 5,374,541, and 5,545,553. The enzymes and substrates can be combined in an initial reaction mixture, or alternatively, the enzymes and reagents for a second glycosyltransferase cycle can be added to the reaction medium once the first glycosyltransferase cycle has neared completion. By conducting two glycosyltransferase cycles in sequence in a single vessel, overall yields are improved over procedures in which an intermediate species is isolated.

Methods of chemical synthesis are described by Zhang et al. (1999) *J. Am. Chem. Soc.*, 121(4): 734–753. Briefly, in this approach, a set of sugar-based building blocks is created with each block preloaded with different protecting groups. The building blocks are ranked by reactivity of each protecting group. A computer program then determines exactly which building blocks must be added to the reaction so that the sequences of reactions from fastest to slowest produces the desired compound.

Kits.

In still another embodiment, this invention provides kits embodying a molehole, a molehole array, a channel, or a channel array of this invention. In preferred embodiments, the kit provides the molehole, molehole array, channel, or channel array comprising two or more conductors in each molehole or channel where the conductors are not attached to a molecule (e.g. a redox active species or a binding partner). Such kits, optionally include one or more molecules (e.g. a redox active molecule, a binding partner) for attachment in the molehole(s) or channel(s).

Certain kits, provide a molecular memory element comprising a molehole array comprising moleholes having redox-active molecules attached to working electrode(s) in the moleholes.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A molecular memory, said memory comprising an electrochemical cell array, said cell array comprising a plurality of nanoscale electrochemical cells wherein a cell comprising said memory is a well having a cross-sectional area less than about 1 micron by 1 micron;

wherein a wall of said well comprises a first electrode and a second electrode said first electrode and said second electrode separated by a non-conductor or semiconductor, wherein the ratio of the surface area of said first electrode exposed to the interior of said well to the surface area of said second electrode exposed to the interior of said well is at least about 2:1; and wherein a redox-active molecule is electrically coupled to said second electrode.

2. The memory of claim 1, wherein said redox-active molecule is a molecule selected from the group consisting of a porphyrinic macrocycle, a metallocene, a linear polyene, a cyclic polyene, a heteroatom-substituted linear polyene, a heteroatom-substituted cyclic polyene, a tetrathiafulvalene, a tetraselenafulvalene, a metal coordination complex, a buckyball, a triarylamine, a 1,4-phenylenediamine, a xanthene, a flavin, a phenazine, a phenothiazine, an acridine, a quinoline, a 2,2'-bipyridyl, a 4,4'-bipyridyl, a tetrathiotetracene, and a peri-bridged naphthalene dichalcogenide.

3. The memory of claim 2, wherein said redox-active molecule is a molecule selected from the group consisting of a porphyrin, an expanded porphyrin, a contracted porphyrin, a ferrocene, a linear porphyrin polymer, a porphyrin sandwich complex, and a porphyrin array.

4. The memory of claim 3, wherein said organic molecule comprises a porphyrinic macrocycle substituted at a β-position or at a meso-position.

5. The memory of claim 1, wherein said ratio is predetermined.

6. The memory of claim 1, wherein said ratio is at least about 5:1.

7. The memory of claim 1, wherein said well has a volume less than about 10 femtoliters ($10 \times 10^{-15}$ L).

8. The memory of claim 1, wherein said array comprises at least 100 wells.

9. The memory of claim 1, wherein the center to center distance between two wells comprising said memory is about 250 nm or less.

10. The memory of claim 1, wherein a plurality of the cells comprising said memory are independently addressable.

11. The memory of claim 1, wherein said first electrode comprises all the walls comprising said well except the bottom wall and, if present, a top wall.

12. The memory of claim 1, wherein said first electrode and said second electrode comprises all the walls comprising said well except the bottom wall and, if present, a top wall.

13. The memory of claim 1, wherein said first and said second electrode are independently selected from the group consisting of copper, silver, gold, platinum, a conducting polymer, aluminum, silicon, germanium, gallium arsenide, ruthenium, titanium and tantalum.

14. The memory of claim 1, wherein said first electrode is a semiconductor.

15. The memory of claim 1, wherein said insulator or semiconductor is an insulator.

16. The memory of claim 15, wherein said insulator is selected from the group consisting of silicon dioxide, silicon nitride.

17. The memory of claim 1, wherein said first electrode is a silver electrode, said second electrode is a gold electrode.

18. The memory of claim 17, wherein said array is formed on a silicon substrate.

19. The memory of claim 17, wherein a plurality of the cells of said memory are independently addressable.

* * * * *